United States Patent
Kim et al.

(10) Patent No.: US 11,504,396 B2
(45) Date of Patent: Nov. 22, 2022

(54) PHARMACEUTICAL COMPOSITION AND METHODS COMPRISING IMMUNE CELLS AND PONATINIB

(71) Applicant: NKMAX Co., Ltd., Gyeonggi-do (KR)

(72) Inventors: Tae-gyun Kim, Gyeonggi-do (KR); Yong-hee Rhee, Gyeonggi-do (KR); Sang-min Oh, Gyeonggi-do (KR)

(73) Assignee: NKMAX Co., Ltd., Gyeonggi-do (KR)

( * ) Notice: Subject to any disclaimer, the term of this patent is extended or adjusted under 35 U.S.C. 154(b) by 546 days.

(21) Appl. No.: 16/471,548

(22) PCT Filed: Dec. 19, 2017

(86) PCT No.: PCT/US2017/067289
§ 371 (c)(1),
(2) Date: Jun. 19, 2019

(87) PCT Pub. No.: WO2018/118907
PCT Pub. Date: Jun. 28, 2018

(65) Prior Publication Data
US 2020/0085870 A1    Mar. 19, 2020

Related U.S. Application Data

(60) Provisional application No. 62/437,620, filed on Dec. 21, 2016.

(51) Int. Cl.
*A61K 35/17* (2015.01)
*A61K 31/5025* (2006.01)
*C12N 5/0783* (2010.01)
*A61K 9/00* (2006.01)

(52) U.S. Cl.
CPC .......... *A61K 35/17* (2013.01); *A61K 31/5025* (2013.01); *C12N 5/0646* (2013.01); *A61K 9/0019* (2013.01); *C12N 2501/15* (2013.01); *C12N 2501/727* (2013.01); *C12N 2501/998* (2013.01); *C12N 2502/1107* (2013.01); *C12N 2502/1114* (2013.01); *C12N 2502/1121* (2013.01)

(58) Field of Classification Search
CPC .............................. A61K 35/17; C12N 5/0646
See application file for complete search history.

(56) References Cited

U.S. PATENT DOCUMENTS

| 9,938,498 | B2 | 4/2018 | Lee et al. |
| 10,590,385 | B2 | 3/2020 | Park et al. |
| 11,066,644 | B2 | 7/2021 | Park et al. |
| 2013/0287688 | A1 | 10/2013 | Jain et al. |
| 2014/0369977 | A1 | 12/2014 | Zhang et al. |
| 2015/0139943 | A1 | 5/2015 | Campana et al. |
| 2015/0152387 | A1 | 6/2015 | Lee et al. |
| 2016/0229901 | A1 | 8/2016 | Merchant |
| 2016/0297821 | A1 | 10/2016 | Stefinovic et al. |
| 2016/0324964 | A1 | 11/2016 | Markovic et al. |
| 2017/0349880 | A1* | 12/2017 | Doucey ............... A61K 31/444 |
| 2018/0223257 | A1 | 8/2018 | Lee et al. |
| 2019/0345449 | A1 | 11/2019 | Park et al. |
| 2020/0172869 | A1 | 6/2020 | Park et al. |
| 2021/0032597 | A1 | 2/2021 | Park et al. |

FOREIGN PATENT DOCUMENTS

| WO | WO 2000/000587 A1 | 1/2000 |
| WO | WO 2004/011673 A1 | 2/2004 |
| WO | WO 2016/096903 A1 | 6/2016 |
| WO | WO 2018/118907 | 6/2018 |
| WO | WO 2019/152663 | 8/2019 |
| WO | WO 2021/108389 | 6/2021 |

OTHER PUBLICATIONS

International Search Report in PCT Application No. PCT/US17/67289, dated Mar. 1, 2018 in 2 pages.
Kaneko, et al., *A report of three patients treated with immunocell therapy with imatinib mesylate*, Anticancer Res. Sep.-Oct. 2004;24(5C):3303-9.
Tran, et al., *TGFβR1 Blockade with Galunisertib (LY2157299) Enhances Anti-Neuroblastoma Activity of Anti-GD2 Antibody Dinutuximab (ch14.18) with Natural Killer Cells*, Clin Cancer Res. Oct. 10, 2016. pii: clincanres.1743.2016.
Raj, et al., *Autologous Immune Enhancement Therapy in Philadelphia Chromosome Positive Acute Lymphoblastic Leukemia*, Indian J Hematol Blood Transfus. Sep. 2014;30(Suppl 1):202-4.
Chen, et al., *Development and dynamics of robust T-cell responses to CML under imatinib treatment*, Blood. Jun. 1, 2008;111(11):5342-9.
Hassold, et al., *Enhancement of natural killer cell effector functions against selected lymphoma and leukemia cell lines by dasatinib*, Int J Cancer. Sep. 15, 2012;131(6):E916-27.

* cited by examiner

*Primary Examiner* — Daniel C Gamett
(74) *Attorney, Agent, or Firm* — Knobbe, Martens, Olson & Bear, LLP

(57) ABSTRACT

Methods and compositions for treating cancer are disclosed. The compositions comprise immune cells pretreated with ponatinib, or immune cells co-administered with ponatinib, where ponatinib promotes survival and anti-cancer cytotoxicity of the immune cells.

25 Claims, 15 Drawing Sheets

Figure 2A
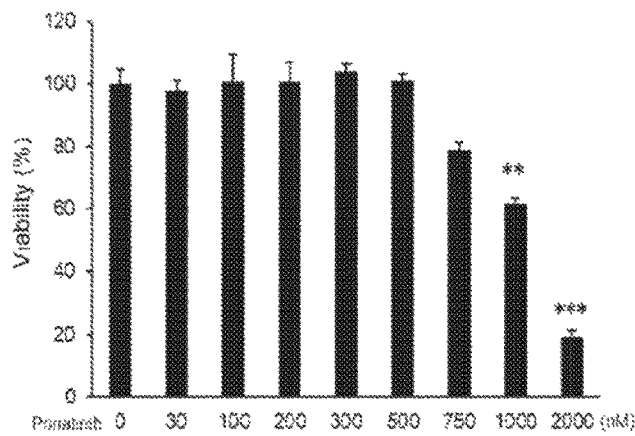
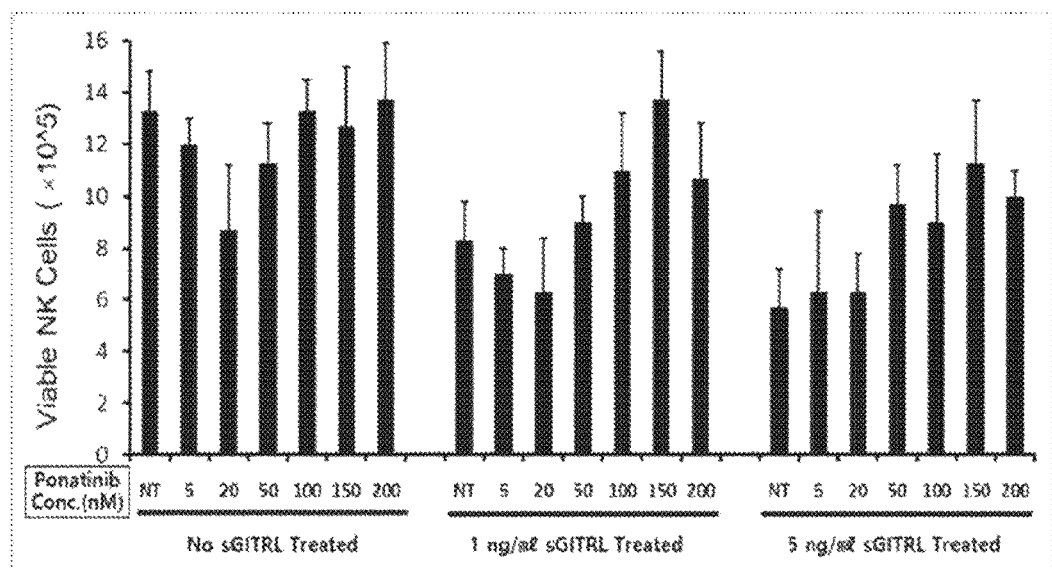
Figure 2B

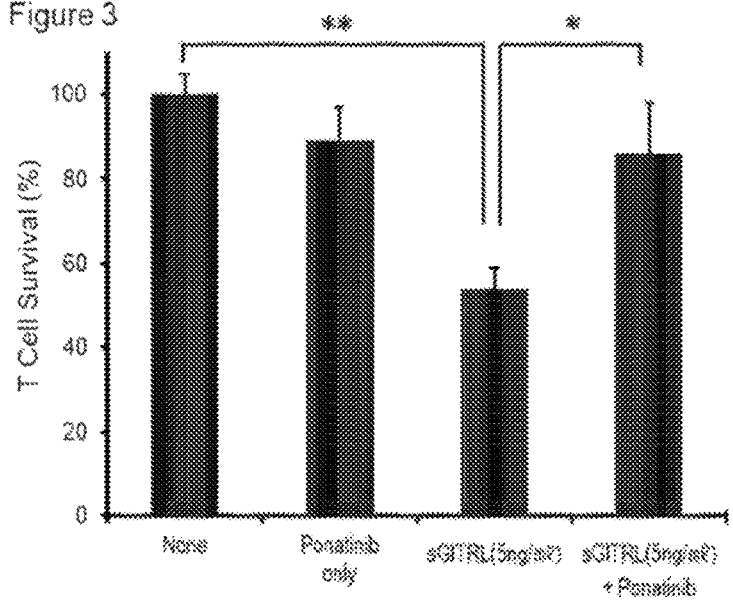

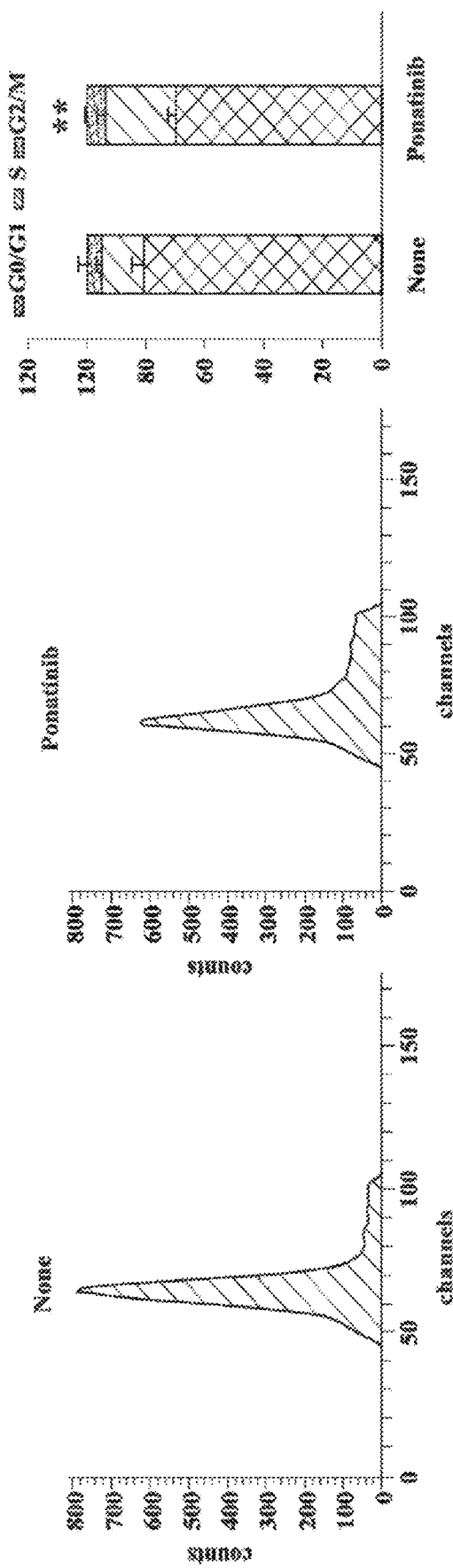

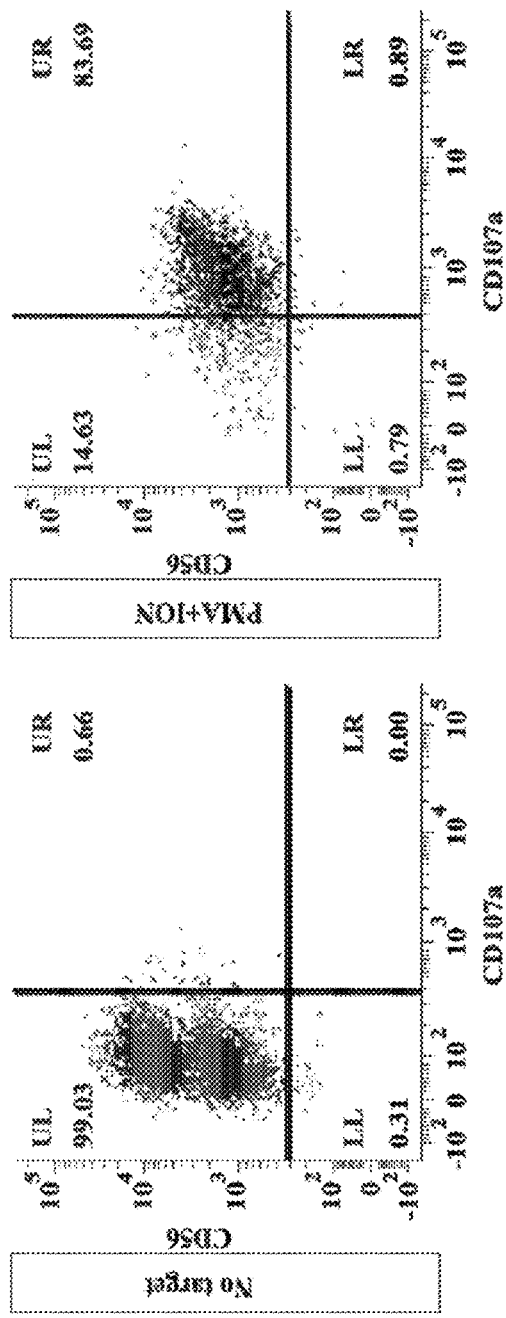

PHARMACEUTICAL COMPOSITION AND METHODS COMPRISING IMMUNE CELLS AND PONATINIB

INCORPORATION BY REFERENCE TO ANY PRIORITY APPLICATIONS

This application is a national stage application of International Patent Application No. PCT/US2017/067289, filed Dec. 19, 2017, which claims the benefit of U.S. Provisional Application No. 62/427,620, filed Dec. 21, 2016, the disclosures of which are hereby incorporated by reference in their entireties.

BACKGROUND

Field

This application is related to methods and compositions for treating tumors, cancers, viral diseases and immune disorders, comprising immune cells along with one or more cell death (apoptosis) inhibitors (e.g., kinase inhibitor, caspase inhibitor, TGF-β receptor inhibitor). This composition enables an effective treatment by improving survival, growth and cytotoxicity of the immune cells.

Description of the Related Art

A human body has immune cells, such as natural killer (NK) cells or T lymphocytes, that are components of the immune system and kill cancer cells or virally infected cells. NK cells are lymphocytes that are part of the innate immune system and kill transformed cells via cytotoxic activity. T lymphocytes are part of the acquired immune system and distinguish between normal and abnormal cells via an antigen-specific receptor.

Immunotherapies are employed, in which immune cells are cultured in vitro to increase their number and activity and then are administered to a patient. Clinical research has been conducted to develop treatments of various diseases using such immune cells, and meaningful results were published during some clinical studies using genetically modified T cells (e.g., chimeric antigen receptor T-cell or CAR-T cells). However, most of clinical studies in which immune cells were cultured and administered to a patient, failed to show sufficient therapeutic effects, partly because administered immune cells did not survive long in the patient's body and partly because cancer cells and virus have various inhibitory mechanisms against immune cells.

For example, it is well known that patients with various types of cancer (e.g., blood cancer) experience inhibition of or decrease in immune cell activity. Blood or body fluids of a cancer patient is known to have a high concentration of various inhibitors of immune cell activity (e.g., cytokine, ligand) produced from cancer cells. In addition, even when lymphocytes are successfully delivered near cancer cells, lymphocytes must survive in a unique microenvironment formed by suppressive immune cells (e.g., regulatory T cells or $T_{reg}$) near cancer cells. For instance, $T_{reg}$ cells in such microenvironment secrete immunosuppressive cytokines (e.g., Transforming Growth Factor-β or TGF-β), which reduce activity of immune effector cell and cause immune cell death.

Viruses employ various strategies to evade or interfere with the immune system. These strategies include transforming or controlling signal transduction, cell death, and/or cell cycle. Viruses typically make use of mechanisms controlling production and activity of cytokines and/or chemokines such as interferons (IFNs) or tumor necrosis factor (TNF). For example, viral infection induces the IFN signaling cascade and eventually the expression of type I IFN, which then results in an anti-viral state in the infected cells. However, many viruses have developed strategies to counteract this mechanism and prevent the production of IFN. In order to modulate or inhibit the IFN signaling cascade in their favor, viruses have found ways to interfere at every single step of the cascade, such as by inducing protein degradation or cleavage, or by mediating protein polyubiquitination. In another example, viruses stimulate infected cells to secrete CD30, a member of the TNF receptor superfamily, which modulates type 1 cytokines (e.g., IFN-γ or IL-12), and thereby inhibits CTL immune responses and inflammatory responses. Different types of viruses have different immunosuppressive functions and targets. Virally produced substances bind to membranes or receptors of immune cells and inhibit immune responses by competitively inhibiting the binding of host substances and/or making infected cells to secret particular proteins. Thus, overcoming immunosuppressive mechanisms of the viruses would provide better therapeutic methods against viral diseases.

Continued efforts have been made to develop anti-cancer or anti-viral therapeutic biologics using immune cells, which are part of immune defense mechanisms unique to a multicellular organism. Strategies are needed to help therapeutic immune cells survive in patient's body and maintain their cytotoxicity for an extended period of time. There are medical needs for compositions for more effective anti-cancer immunotherapies using combinations of conventionally proliferated immune cells and various substances that inhibit cell death (also referred to as apoptosis) of those immune cells.

SUMMARY

This application is related to methods and pharmaceutical compositions for treating pathological cell proliferation such as tumors and cancers, or diseases related to viral infection and immune disorders, comprising NK cells or T cells along with at least one cell death inhibitor, such as ponatinib. These compositions were shown by a number of experimental studies to increase the survival period of immune cells in a cell death-inducing condition similar to that in cancer patients and in the blood of experimental mouse body. Furthermore, the composition could increase anti-cancer activity and cytotoxicity against various cancer cells and virally infected cells as compared with other kinase inhibitors.

An embodiment provides therapeutic compositions for treating tumors or cancers, comprising NK cells or T cells treated with ponatinib, a kinase inhibitor. Other embodiments provide a first therapeutic composition (Therapeutic Composition 1) for treating tumors and cancers, comprising immune cells and an effective amount of Ponatinib.

An embodiment provides a pharmaceutical composition for treating cancers, the pharmaceutical composition comprising immune cells and an effective amount of ponatinib. The immune cells in the embodiment may comprise at least one of NK cells, T cells, B cells, dendritic cells, or macrophages. The NK cells in the embodiment may comprise at least one of NK cells cultured with cytokines; NK cells co-cultured with cytokines and irradiated human peripheral blood mononuclear cells (PBMC); NK cells co-cultured with established cell line(s) such as transformed lymphocytes (e.g., LCL cells, and/or KL-1 cells and/or K562 cells), or genetically engineered feeder cells; or genetically engineered CAR-NK cells. The T cells in the embodiment may comprise at least one of T cells isolated from PBMC and cultured with cytokines; T cells extracted near tumors; T cells treated with activators (e.g., tumor antigen peptide and/or tumor lysates); or genetically engineered CAR-T cells. The kinase inhibitor in the embodiment may comprise ponatinib. The concentration of the kinase inhibitor in the embodiment may be from about 1 nM to about 1 µM.

An embodiment provides a method for treating cancer, the method comprising administering to a patient in need thereof a therapeutically effective amount of a pharmaceutical composition comprising immune cells and ponatinib.

An "effective amount" of ponatinib is defined as an amount sufficient to suppress immune cell death induced by cancer immunosuppressant pathways (e.g., TNFRF, Fas, or TGF-β pathways) as well as to enhance anti-cancer activity of immune cells.

Any features, structures, or steps disclosed herein can be replaced with or combined with any other features, structures, or steps disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

In a first embodiment, a pharmaceutical composition for treating cancer is disclosed. The pharmaceutical composition includes immune cells and ponatinib or a pharmaceutically acceptable salt or derivative thereof.

In certain embodiments, the immune cells include at least one of NK cells, T cells, B cells, dendritic cells, and macrophages. In a variation, the immune cells are NK cells, where the NK cells include at least one of NK cells cultured with cytokines, NK cells co-cultured with cytokines and irradiated human peripheral blood mononuclear cells (PBMC), NK cells co-cultured with established cell line(s) or genetically engineered feeder cells or both, and genetically engineered CAR-NK cells. The established cell lines may be transformed lymphocyte cells selected from LCL cells, KL-1 cells, or K562 cells.

In certain embodiments, the immune cells include T cells, where the T cells comprise at least one of T cells isolated from peripheral blood mononuclear cells (PBMC) and cultured with cytokines, T cells extracted near tumors, T cells treated with activators, and genetically engineered CAR-T cells.

In one embodiment of the pharmaceutical composition, the concentration of ponatinib or pharmaceutically acceptable salt or derivative thereof is from about 1 nM to 1 µM.

In one embodiment of the pharmaceutical composition, the immune cells are pre-treated with an effective amount of ponatinib or pharmaceutically acceptable salt or derivative thereof. In another embodiment, the immune cells are pre-treated with ponatinib or pharmaceutically acceptable salt or derivative thereof at a concentration of about 1 nM to 1 µM.

In a second embodiment, a pharmaceutical composition for treating cancer is disclosed. The pharmaceutical composition includes immune cells, which have been pre-treated in vitro with an effective concentration of ponatinib or a pharmaceutically acceptable salt or derivative thereof. The immune cells may include at least one of NK cells, T cells, B cells, dendritic cells, and macrophages. In a variation, the immune cells may include NK cells, where the NK cells may comprise at least one of NK cells cultured with cytokines, NK cells co-cultured with cytokines and irradiated human peripheral blood mononuclear cells (PBMC), NK cells co-cultured with established cell line(s) such as transformed lymphocytes (e.g., LCL cells, and/or KL-1 cells, and/or K562 cells) or genetically engineered feeder cells, and genetically engineered CAR-NK cells.

In one embodiment, the immune cells comprise T cells, where the T cells include at least one of T cells isolated from peripheral blood mononuclear cells (PBMC) and cultured with cytokines, T cells extracted near tumors, T cells treated with activators, and genetically engineered CAR-T cells.

The effective concentration of ponatinib or a pharmaceutically acceptable salt or other derivative thereof is about 1 nM to 1 µM.

A method for treating cancer is disclosed in accordance with another embodiment. The method includes: treating immune cells with ponatinib or pharmaceutically acceptable salt or derivative thereof; and administering an effective amount of a pharmaceutical composition comprising the treated immune cells to a patient.

In a variation, the method may also include collecting immune cells from a subject before treating the immune cells with ponatinib. The subject may be the patient.

In another variation, the method may include proliferating immune cells in vitro before treating immune cells with ponatinib or a pharmaceutically acceptable salt or other derivative thereof. The step of administering the pharmaceutical composition may include intravenously injecting the pharmaceutical composition. The immune cells may include at least one of NK cells, T cells, B cells, dendritic cells, and macrophages.

In one embodiment of the method, the concentration of ponatinib or pharmaceutically acceptable salt thereof is about 1 nM to 1 µM.

In another embodiment of the method, the pharmaceutical composition may comprise about $10^5$ to about $10^{10}$ treated immune cells per dose.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 2A is a graph showing the viability of NK cells treated with various concentrations of ponatinib.

FIG. 2B is a graph showing the number of viable NK cells pretreated with various concentration of ponatinib, followed by treatment with sGITRL.

FIG. 3 is a graph showing survival percentages of T cells pretreated with or without ponatinib, followed by treatment with sGITRL.

FIGS. 12A-C illustrate flow cytometry results showing the fraction distributed at G0/G1, S and G2/M phases in NK cells treated with or without ponatinib.

FIGS. 13A-D illustrate flow cytometry results showing ponatinib pretreated NK cell degranulation against K562 targets.

DETAILED DESCRIPTION

Figure 1A:
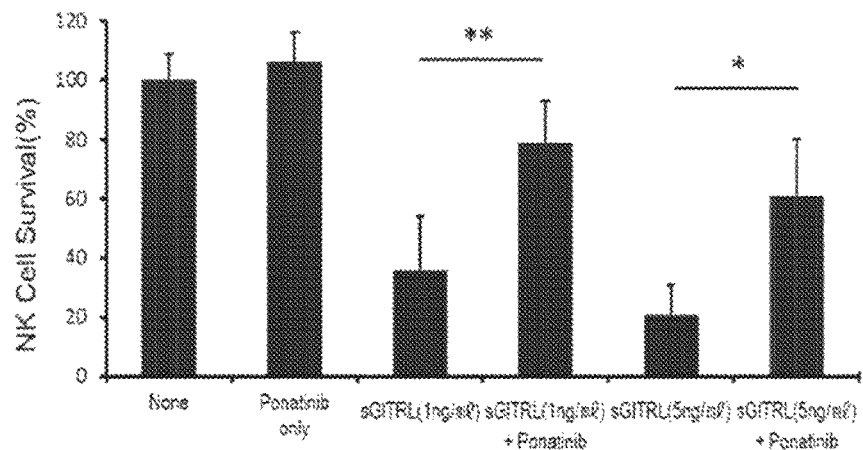
FIG. 1A is a graph showing survival percentages of NK cells pretreated with or without ponatinib, followed by treatment with soluble glucocorticoid-induced TNFR-related protein (sGITRL).

Details regarding several illustrative embodiments for implementing the compositions and methods described herein are described below with reference to the figures. The invention is not limited to these described embodiments.

A study found that blood samples of about 56% of colon cancer patients, about 50% of stomach cancer patients, about 56% of lung cancer patients, and about 40% of acute myeloid leukemia (AML) patients had a high concentration of soluble Glucocorticoid-Induced TNF Receptor-Related Protein Ligand (sGITRL) spontaneously released by cancer cells. sGITRL is known to diminish anti-tumor activity of immune effector cells such as NK cells or T cells and impair interferon-gamma (IFN-γ) production by NK cells. However, sGITRL is not found in the blood of healthy people.

It was also shown that blood of stomach cancer patients has NK cells with higher Fas expression level and a higher proportion of apoptotic circulating NK cells than that of normal people. It was found that the proportion of apoptotic circulating NK cells decreases after cancer surgery in a statistically significant manner.

Blood of cancer patients is known to have a higher concentration of TGF-β, which significantly diminishes immune activity of NK cells and T cells, than that of normal people. In addition, in blood of cancer patients, membrane-bound TGF-β is expressed on the surface of regulatory T cells to drastically decrease the effector function and cytotoxicity of NK cells and inhibits expression of cytotoxicity-related receptors (e.g., NKG2D) on NK cell membrane.

Strategies to maintain and optimize survival and activity of immune cells, such as NK cells or T cells, have been developed. For example, research on therapeutic antibodies has focused on improving their efficacy against cancer cells by stimulating cytotoxicity or blocking inhibitory receptors using a checkpoint inhibitor (e.g., anti-PD-1 antibody or anti-CTLA-4 antibody). However, efficacy of a couple of newly developed therapeutic antibodies is limited to a small population of patients, and a large portion of cancer patients still need novel therapeutic agents.

Disclosed herein are several therapeutic compositions for treating tumors, cancers, viral diseases and/or immune disorders, the compositions comprising immune cells (e.g., NK cells, T cells, B cells, dendritic cells, macrophages, etc.) in combination with one or more agents that promotes immune cell survival and/or inhibits immune cell apoptosis.

A first therapeutic composition (Therapeutic Composition 1) according to some embodiments comprises immune cells and an effective amount of a kinase inhibitor. A second therapeutic composition (Therapeutic Composition 2) according to some embodiments comprises immune cells and an effective amount of a caspase inhibitor. A third therapeutic composition (Therapeutic Composition 3) according to some embodiments comprises immune cells and an effective amount of a TGF-β receptor inhibitor. A fourth therapeutic composition (Therapeutic Composition 4) according to some embodiments comprises immune cells, an effective amount of a kinase inhibitor, and an effective amount of a caspase inhibitor. A fifth therapeutic composition (Therapeutic Composition 5) according to some embodiments comprises immune cells, an effective amount of a kinase inhibitor, and an effective amount of a TGF-β receptor inhibitor. A sixth therapeutic composition (Therapeutic Composition 6) according to some embodiments comprises immune cells, an effective amount of a caspase inhibitor, and an effective amount of a TGF-β receptor inhibitor. A seventh therapeutic composition (Therapeutic Composition 7) according to some embodiments comprises immune cells, an effective amount of a kinase inhibitor, an effective amount of a caspase inhibitor, and an effective amount of a TGF-β receptor inhibitor. In some embodiments of the above enumerated Therapeutic Compositions, the immune cells were pretreated with one or more of the kinase inhibitor, caspase inhibitor and TGF-β receptor inhibitor. In some embodiments of the above enumerated Therapeutic Compositions, the immune cells are provided together with the one or more kinase inhibitor, caspase inhibitor and TGF-β receptor inhibitor. In other embodiments of the above enumerated Therapeutic Compositions, the immune cells are pretreated in vitro with, and/or provided together with, the one or more kinase inhibitor, caspase inhibitor and TGF-β receptor inhibitor.

Methods for treating tumors, cancers, viral diseases and/or immune disorders are also disclosed. In some embodiments, the method may comprise administering to a patient in need thereof an effective amount of any of the various embodiments of the above enumerated Therapeutic Compositions 1-7 (i.e., immune cells pretreated with one or more inhibitors, immune cells co-administered with one or more inhibitors, or immune cells both pretreated with and co-administered with one or more inhibitors).

The therapeutic compositions described in this section or elsewhere in the specification comprising immune cells and an effective amount of various compounds may show higher survival rate, stronger anti-cancer cytotoxicity, and anti-viral immune response. Accordingly, these therapeutic compositions may be useful for treating cancer. Cancer is used herein to include tumors or solid cancers (e.g., stomach cancer, colon cancer, prostate cancer, lung cancer, breast cancer, liver cancer, kidney cancer, pancreatic cancer, gall bladder cancer, cholangiocarcinoma [bile duct cancer], glioblastoma, gastrointestinal cancer, endometrial cancer, bladder cancer, etc.) as well as blood cancers (e.g., leukemia, myeloma, lymphoma, myeloid leukemia, acute lymphoblastic leukemia, acute myeloid leukemia, and myelodysplastic syndrome, etc.). The therapeutic compositions may also be useful in treating infectious diseases (e.g., hepatitis B, hepatitis C, pneumonia, tuberculosis, etc.) and immune diseases (e.g., autoimmune diseases, atopic dermatitis, psoriasis, chronic inflammation, rheumatoid arthritis, osteoarthritis, cardiovascular disease, etc.).

In addition to the above-mentioned list of cancers, methods and compositions disclosed in this application may be used for other types of cancers comprising: skin cancer (e.g., squamous cell carcinoma, basal cell cancer, and melanoma), prostate cancer, brain cancer, nervous system tumors, head and neck cancer, testicular cancer, lung cancer, liver cancer, kidney cancer, osteosarcoma (bone cancer), endocrine cancer (e.g., thyroid cancer and pituitary cancer), and lymphoma (e.g., Hodgkin's lymphoma and non-Hodgkin's lymphoma). Other examples of cancers that could be treated by the above-mentioned methods and compositions comprise fibrosarcoma, neuroectodermal tumor, mesothelioma, epidermoid carcinoma, and Kaposi sarcoma.

Cancer and Immune Cells

Immune cells have been developed as cancer drug, in which immune cells are cultured and proliferated in vitro and administered to patient's body. Many clinical studies with immune cells (except for a small number of genetically engineered CAR-T cells) generally showed limited tumor responsiveness and low anti-cancer activity. This is because many immunosuppressive substances released by tumors of a cancer patient inhibit the administered immune cells. In order to overcome such a limitation, strategies such as treating immune cells with activation receptor binding proteins or antibodies blocking inhibitory receptors, are required to optimize anti-cancer immune activity and stimulate immune cell activation. Another potentially useful treatment strategy may include treating immune cells with compounds to enhance therapeutic efficacy against cancer, tumors and viral disease.

It was observed by the present inventors that when immune effector cells such as NK cells or T cells in the body of a cancer patient were exposed to signal transduction substance for tumor necrosis factor receptor (TNFR) ligands, such as sGITRL, the viability of immune cells was greatly reduced. This was also observed when immune effector cells were treated with TGF-β or Fas ligand (Fas-L), which is mostly secreted from immune-suppressive cells (e.g., $T_{reg}$) in cancer patients. It was also shown by the inventors that pretreating immune effector cells with multi-targeted kinase inhibitor, increased immune cell's survival rate and anti-cancer activity by blocking cell death-related signaling pathways.

As mentioned above, several studies have reported the observation of elevated sGITRL levels in patients with various types of cancer. When serum sGITRL level of colon cancer patients (n=25) was measured using the ELISA method, 56% of the patients had positive serum sGITRL levels over the limit of detection (LOD), with an average of 1.62 ng/ml and a range from 0.77 to 3.47 ng/ml. For lung cancer patients (n=27), 56% of the patients had positive serum sGITRL levels over LOD, with an average of 1.86 ng/ml and a range from 0.13 to 3.00 ng/ml. For gastric cancer patients (n=8), 50% of the patients had positive serum sGITRL levels over LOD, with an average of 0.67 ng/ml and a range from 0.13 to 1.24 ng/ml. For acute myeloid leukemia patients (n=25), 40% of the patients had positive serum sGITRL levels over LOD, with an average of 1.73 ng/ml and a range from 0.15 to 7.37 ng/ml.

The concentrations of sGITRL (1 or 5 ng/mL; FIG. 1A) used in the non-limiting examples according to some embodiments are similar to previously reported concentrations of sGITRL in the serum of cancer patients. Inventors of this application observed that when immune cells were treated with sGITRL at a concentration level similar to one that can be found in blood or body fluid of cancer patients, the immune cells rapidly underwent cell death within a day or two. This observation provides explanation for the limited anti-cancer activities of immune cell therapeutic agents or immune system activators, which have been used in clinical studies for cancer patients.

The present inventors showed that pretreatment of NK cells or T cells with inhibitory compounds against TNFR or TGF-β signaling pathway mechanisms inhibited their cell deaths induced by cell death-inducing substances, such as sGITRL, TGF-β, or Fas-L. The inventors also showed that NK cells pretreated with inhibitory compounds against TNFR or TGF-β signaling pathway had a higher anti-cancer activity against blood and solid cancers than untreated NK cells.

In some circumstances, if the above mentioned inhibitory compounds against TNFR or TGF-β signaling pathway mechanisms are delivered systemically by conventional methods (e.g., oral or intravenous administration) in order to inhibit cell death of immune cells in cancer patients, these inhibitory compounds may have the undesired effect of also inhibiting the cytotoxic actions of the immune cells, and thereby suppress cell death of the cancer cells. Immune effectors cells (e.g., NK cells) secrete stimulatory cytotoxic substances such as Fas-L, TNF-α, and TRAIL that stimulate cancer cell death and result in anti-cancer or anti-viral therapeutic effects. Therefore, if cancer cells are exposed to the inhibitory compounds against TNFR or TGF-β signaling pathway mechanisms, these inhibitory compounds may disrupt the functions of the stimulatory cytotoxic substances and block cancer cell death.

Activated NK cells are known to show highly elevated Fas expression and present various kinds of TNF Receptor (TNFR) family proteins (e.g., TNFR Super Family 18 or TNFRSF18). Due to these receptors, cell death-inducing substances such as Fas-L or TNF-α that are secreted by NK cells to kill cancer cells may also damage the NK cells themselves (e.g., NK cells may lose cytotoxicity) or induce cell death of the NK cells. This is consistent with studies reporting that activated NK cells rapidly underwent apoptosis after attacking tumor or cancer cells. Thus, compared to systemic administration (e.g., oral or intravenous administration) of inhibitory compounds against cell death, pretreatment of therapeutic immune effector cells with the inhibitory compounds in vitro culture may protect the immune effector cells from various cell death signaling while increasing their subsequent cytotoxicity against cancer cells when administered in vivo.

Viral Diseases and Immune Cells

In case of viral diseases, viruses activate many mechanisms that inhibit or evade the immune response of host cells of an infected patient. If anti-viral compounds do not completely remove virally infected cells and leave virus inside the patient's body, acutely or chronically, the anti-viral compounds might not be effective to all patients, or viral infection might relapse. In this case, improving survival rate and anti-viral activity of immune cells administered to a patient would provide therapeutic benefits for effectively treating viral diseases.

NS1 protein of influenza virus is known as a suppressor of innate and adaptive immunity as well as a virulence factor. Type 1 interferon (T1 IFN) is secreted from infected cells and induces anti-viral activities by stimulating NK cell functions and modulating innate immune responses. However, influenza viruses inhibit the T1 IFN system of the infected cells and suppress the activities of the host cells and immune cells. Infection of some other types of viruses was reported to suppress IFN expression by disrupting signal transduction pathways of interferon regulatory factor (IRF) and NF-kB conducted by TIR-domain-containing adapter-inducing interferon-β (TRIF). Further, viruses suppress immune responses mediated by IFN via various other mechanisms. These mechanisms include inducing disintegration of interferon-α/β receptor (IFNAR) on cell membrane surface; inhibiting phosphorylation of STAT (Signal Transducer and Activator of Transcription; downstream signal transduction pathway of IFNAR), ubiquitinylation, and degradation; and expressing suppressors of cytokine signaling (SOCS), which are known as negative regulators of the JAK-STAT signal transduction pathway.

If virally infected cells that underwent the above-mentioned mechanisms are not completely removed from patients, and viruses survive in the patients' body acutely or chronically, synthetically made anti-viral therapeutic agents may not be able to treat all patients with viral diseases, and viral diseases may relapse after the treatment with such therapeutic agents. In these cases, greater killing activities against infected cells and/or greater survival rate of immune cells administered to patients for treatment of viral diseases will provide therapeutic benefits.

Treatment of Immune Cells with Inhibitory Compounds

The above-mentioned methods and compositions according to some embodiments can be clinically applied for greater cytotoxic activity and survival rate of immune cells. In some embodiments, a pharmaceutical composition for treating tumors, cancers, viral diseases and immune disorders may comprise immune cells (e.g. NK cells, T cells, B cells, dendritic cells, macrophages, etc.) along with one or more cell death (apoptosis) inhibitors. In some embodiments, the immune cells may have been pre-treated with the one or more cell death inhibitors. In some embodiments, a method for treating tumors, cancers, viral diseases and immune disorders may comprise: first separating autologous or allogenic immune effector cells (e.g. NK cells, T cells, B cells, dendritic cells, macrophages, etc.); proliferating and culturing these cells in vitro; treating the proliferated or cultured cells with one or more of above-mentioned cell death inhibitors, alone or combined, in a pharmaceutically effective concentration; administering (e.g., intravenously injecting, etc.) the treated cells to a patient with tumor, cancer, viral infection diseases, or immune diseases, or any subcombination of these steps. In some embodiments, the immune cells treated with the inhibitory compounds may be provided as a pharmaceutical composition.

In some embodiments, the immune cells may be treated with one or more of above-mentioned inhibitory compounds. In one example, PBMCs were prepared from peripheral blood using Ficoll-Plaque PLUS and washed twice with PBS. Feeder lines were gamma-irradiated and co-cultured with PBMCs in RPMI-1640 media with 10% FBS plus recombinant human IL-2. On day 6, 10, 14 expanded NK cells were counted and transferred to culture flasks at a concentration of 0.1~1.0×106 cells/mL. To determine the pretreatment effects of inhibitory compounds on NK cells, NK cells were incubated with 0~2,000 nM of inhibitory compounds on day 12 or 13. On day 14, NK cells were washed 3 times with PBS and analyzed.

In some embodiments, the inhibitory compounds may include at least one of a kinase inhibitor, a TGF-β receptor inhibitor, and a caspase inhibitor.

Target Diseases

As discussed above, a therapeutic composition comprising immune cells (e.g. NK cells, T cells, B cells, dendritic cells, macrophages, etc.) along with one or more cell death (apoptosis) inhibitors, and/or immune cells pre-treated with the cell death inhibitors may show higher survival and growth rates and stronger anti-cancer cytotoxicity than immune cells alone. Accordingly, such therapeutic compositions may be useful for treating various diseases, including cancer—solid cancers/tumors (e.g., stomach cancer, colon cancer, prostate cancer, lung cancer, breast cancer, liver cancer, kidney cancer, pancreatic cancer, gallbladder cancer, cholangiocarcinoma [bile duct cancer], glioblastoma, etc.), blood cancers (e.g., leukemia, myeloma, lymphoma, etc.), infectious diseases (e.g., hepatitis B, hepatitis C, pneumonia, tuberculosis, etc.), and immune diseases (e.g., autoimmune diseases, atopic dermatitis, psoriasis, chronic inflammation, rheumatoid arthritis, osteoarthritis, cardiovascular disease, etc.).

Types of Immune Cells

As described above, immune cells may be autologous or allogenic. In some embodiments, immune cells may comprise NK cells. Non-limiting examples of NK cells include, and are not limited to, the followings: NK cells cultured with cytokines; NK cells co-cultured with cytokines and irradiated human peripheral blood mononuclear cells (PBMC); NK cells co-cultured with established cell line(s) such as transformed lymphocytes (e.g., LCL cells, and/or K562 cells), or genetically engineered feeder cells; and genetically engineered CAR-NK cells. See e.g., Pittari G, Front Immunol. 6: 230, 2015; Granzin M, Front Immunol. 8: 458, 2017; incorporated in their entireties by reference thereto.

In some embodiments, immune cells may comprise T cells. Non-limiting examples of T cells include, and are not limited to, the followings: T cells isolated from peripheral blood mononuclear cells (PBMC) and cultured with cytokines; T cells extracted near tumors and/or treated with activators; and genetically engineered CAR-T cells. See e.g., Hartmann J, EMBO Mol Med. 9: 1183, 2017; incorporated in its entirety by reference thereto.

In some embodiments, immune cells may comprise other immune cells, such as, B cells, dendritic cells, and macrophages. Any of these immune cells may be administered to patients in the amount of about 1 to about $10^{12}$ cells per dose, about 10 to about $10^{11}$ cells per dose, about $10^2$ to about $10^{10}$ cells per dose, about $10^3$ to about $10^9$ cells per dose, about $10^4$ to about $10^8$ cells per dose, or about $10^5$ to about $10^7$ cells per dose; these ranges are non-limiting In one embodiment, a pharmaceutical composition may comprise about $10^5$ to about $10^{10}$ pre-treated immune cells per dose.

Types of Cell Death (Apoptosis) Inhibitors

In some embodiments, cell death inhibiting compounds may include TNFSF-related kinase inhibitors. Non-limiting examples of TNFSF-related kinase inhibitors include, and are not limited to, ponatinib, pazopanib, necrostatin-1, imatinib, nilotinib, dasatinib, vandetanib, birinapant, bosutinib and pharmaceutically acceptable salts or other derivatives thereof. These kinase inhibitors may be used to treat the immune cells at concentrations ranging from about 0.1 nM to about 10 μM, from about 1 nM to about 1 μM, or from about 10 nM to about 1 μM; these ranges are non-limiting.

The phrase, "pharmaceutically acceptable derivative", as used herein, denotes any structural analog of a compound, ester or any other adduct or derivative which, upon administration to a patient, is capable of providing (directly or indirectly) a compound as otherwise described herein, or a metabolite or residue thereof. A derivative can differ in one or more atoms, functional groups, or substructures, which are replaced with other atoms, groups, or substructures. Such structural analogs retain similar biological activity and similar pharmacokinetic properties. Additionally, as used herein, the term "pharmaceutically acceptable ester" refers preferably to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. Obviously, esters can be formed with a hydroxyl or carboxylic acid group of the compound of the invention.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the isolation and purification of the compounds of the invention, or separately by reacting the free base or free acid of a compound of the invention with a suitable base or acid, respectively. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide. 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In some embodiments, cell death inhibiting compounds may include one or more caspase inhibitors. Non-limiting examples of caspase inhibitors include, and are not limited to, Caspase-8 inhibitors, Caspase-3 inhibitors, Caspase-10 inhibitors, General Caspase inhibitors, and Bax inhibitors. These caspase inhibitors may be used to treat the immune cells at concentrations ranging from about 1 nM to about 100 μM, from about 10 nM to about 10 μM, or from about 100 nM to about 1 μM; these ranges are non-limiting.

In some embodiments, cell death inhibiting compounds may include one or more TGF-β receptor inhibitors. Non-limiting examples of TGF-β receptor inhibitors include, and are not limited to, LY-2157299, SB431542, and A 83-01. These TGF-β receptor inhibitors may be used to treat the immune cells at concentrations ranging from about 0.5 nM to about 50 μM, from about 5 nM to about 5 μM, or from about 50 nM to about 500 nM; these ranges are non-limiting.

Kinase Inhibitors Treatment of Immune Cells

Kinase inhibitors, above mentioned, were developed as stand-alone therapeutic composition in the form of oral or injection medication for a patient (e.g., cancer patient, etc.). This medication directly acts on cancer cells by inhibiting one or more signaling pathways (e.g., EGFR) that mediate kinase activation necessary for cancer cell growth.

Tyrosine kinase inhibitors (TKIs) are inhibitors of tyrosine kinases that are responsible for the activation of many proteins by signal transduction cascades in multiple cellular processes and have a crucial role in tumor development and progression. Therefore, TKIs have been developed as direct antitumor agents to inhibit tumor growth and/or to induce cancer cell death. Important TKIs include imatinib (Gleevec®), nilotinib (Tasigna®), and dasatinib (Sprycel®) and multi-target TKIs like sunitinib (Sutent®) and sorafenib (Nexavar®). TKIs are known to have inhibitory or activatory effects on the function of immune cells including NK cells and T cells.

In vivo and in vitro studies showed direct inhibitory effects and indirect activatory or inhibitory effects on NK cell function via modification of markers on tumor cells by TKI-treatment (Krieg and Ullrich, Front Immunol 3: 1-10, 2013). Direct exposure of human NK cells with pharmacological doses of imatinib had no impact on NK cytotoxicity or cytokine production, whereas nilotinib negatively influenced cytokine production and dasatinib additionally abrogated cytotoxicity in vitro. The direct modulation of NK cells by dasatinib was apparently based on its impact on signaling cascades preventing phosphorylation of PI-3 kinase and ERK1/2. Interestingly, inhibition by dasatinib seemed to be reversible as washing NK cells mainly restored cytotoxicity.

Imatinib treatment can indirectly augment the NK cell-mediated antitumor effects in vivo through acting on dendritic cells to promote NK cell activation (Borg et al., J Clin Invest 114: 379-88, 2004). When combined with IL-2, imatinib treatment could enhance antitumor effects against melanoma lung metastasis in vivo, as compared with either agent alone. Administration of depleting NK1.1-specific monoclonal antibody completely abrogated the tumoricidal activity induced by the combination of imatinib and IL-2, suggesting an indirect role for NK1.1-expressing dendritic cells in the antitumor effects (Taieb et al., Nat Med 12(2): 214-219, 2006).

Analyses with resting and IL-2-activated NK cells revealed that the protein kinase inhibitors (PKIs) Sunitinib and Sorafenib concentration dependently inhibited cytotoxicity and IFN-γ production of NK cells in response to tumor targets. And this was due to impaired PI-3 kinase and ERK phosphorylation which directly controls NK cell reactivity (Krusch et al., J Immunol 183: 8286-94, 2009).

Figure 6A:
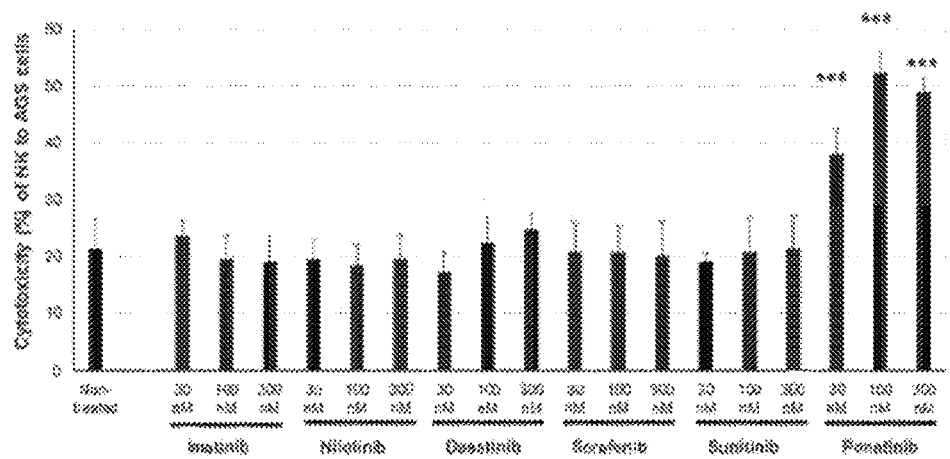
FIGS. 6A-B are graphs showing cytotoxic activity of NK cells pretreated with various kinase inhibitors against cancer cells (AGS and MDA-MB-231 cells).
Figure 6B:
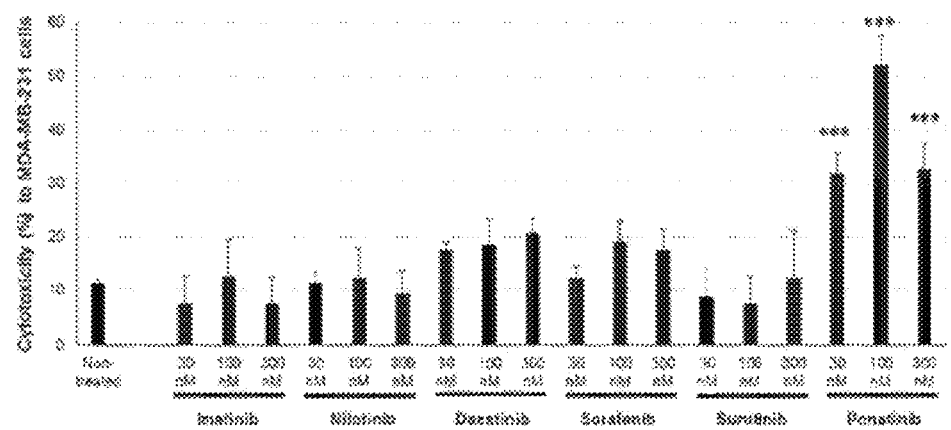

PKIs have been reported to have various effects on the activity of immune cells, including NK cells. The inventors treated various PKIs including TKIs or multi-target kinase inhibitors into NK cells and examined whether they influence on the anti-cancer effect of NK cells when co-cultured with multiple cancer cell lines. As shown in FIGS. 6A-B, anti-cancer cytotoxicity against AGS (the stomach cancer cell line) and MDA-MB-231 (the breast cancer cell line) cells was significantly elevated in NK cells pretreated with ponatinib compared to NK cells untreated. In contrast, pretreatment of NK cells with other kinase inhibitors imatinib, nilotinib, dasatinib, sorafenib and sunitinib did not show any differences in anti-cancer cytotoxicity in any concentrations (30, 100 and 300 μM) compared to untreated NK cells.

Treating with Ponatinib

Ponatinib is a multi-targeted tyrosine kinase inhibitor and its systematic (IUPAC) name is 3-(2-imidazo[1,2-b]pyridazin-3-ylethynyl)-4-methyl-N-[4-[(4-methylpiperazin-1-yl)methyl]-3-(trifluoromethyl)phenyl]benzamide. Ponatinib tablet for oral use (ICLUSIG® manufactured by ARIAD Pharmaceuticals, Inc.) is approved for treatment of chronic myeloid leukemia and Philadelphia chromosome-positive acute lymphoblastic leukemia (O'Hare et al., Cancer Cell 6 (5): 401-12, 2009; Cortes et al., N Engl J Med 367: 2075-88, 2012). This BCR-ABL inhibitor is used as second-line treatment for patients who have acquired resistance to standard therapy. As described herein, the term "ponatinib" may refer to ponatinib, pharmaceutically acceptable salts, or other pharmaceutically acceptable derivatives thereof, and these terms may be used interchangeably. See e.g., Thomas M, Bioorg Med Chem Lett. 21(12): 3743-8, 2011; incorporated herein in its entirety by reference thereto.

In addition, NK cells pretreated with ponatinib showed higher anti-cancer cytotoxicity against SNU-245 (the biliary tract cancer cell line) and SNU-387 (the liver cancer cell line) than did untreated NK cells. But, as shown in FIG. 7 and described further below, pretreatment of NK cells with other kinase inhibitors imatinib, nilotinib, bosutinib, pazopanib, vandetanib, sorafenib, sunitinib, dasatinib imatinib, nilotinib, dasatinib, sorafenib and sunitinib did not increase anti-cancer cytotoxicity of NK cells, except for slightly increased anticancer activity with dasatinib in SNU245 cells and with pazopanib in SNU-387 cells.

Figures 8A, 8B, 8C:
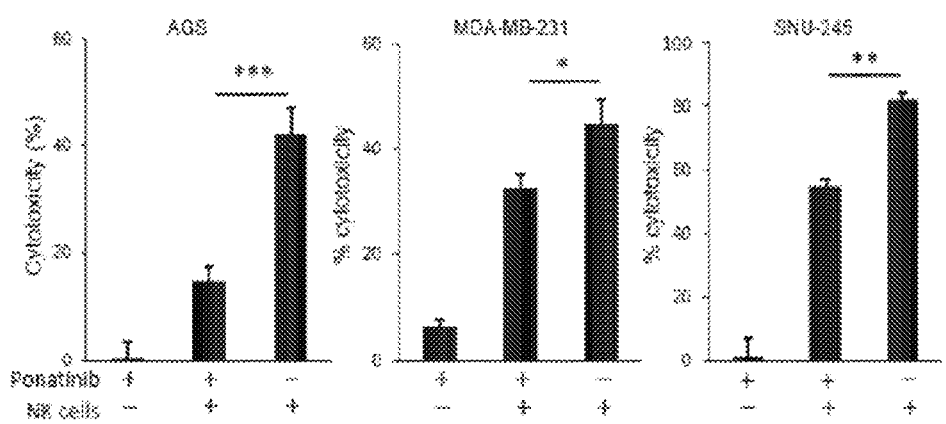
FIGS. 8A-C are graphs showing cytotoxic activity of ponatinib only and NK cells pretreated with or without ponatinib against various cancer cell lines (AGS, MDA-MB-231, and SNU-245).

To determine whether the enhanced anti-cancer cytotoxicity of ponatinib is mediated through NK cell activation or by ponatinib alone, cancer cells were treated with ponatinib alone or with NK cells pretreated with ponatinib. As shown in FIGS. 8A-C and described further below, anti-cancer cytotoxicity was shown by NK cells pretreated with or without ponatinib, but not shown by ponatinib treatment alone, indicating that ponatinib has an anti-cancer cytotoxic activity only through the activation of NK cells' cytotoxic activity.

Figure 1B:
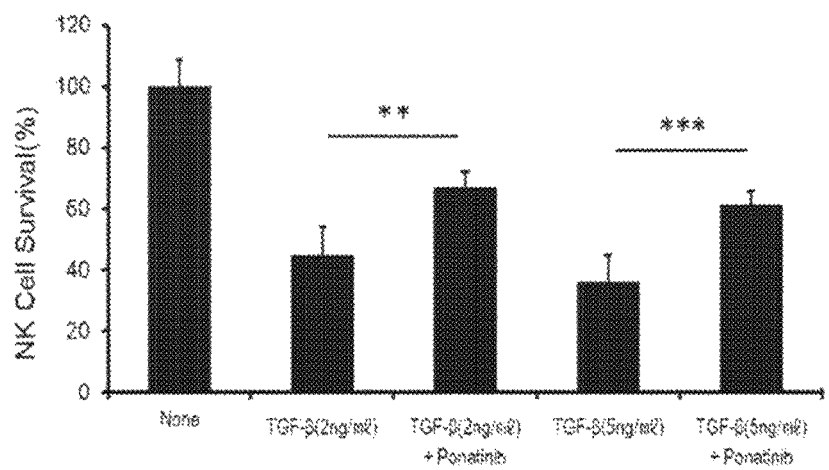
FIG. 1B is a graph showing survival percentages of NK cells pretreated with or without ponatinib, followed by treatment with Transforming Growth Factor-β (TGF-β).
Figure 1C:
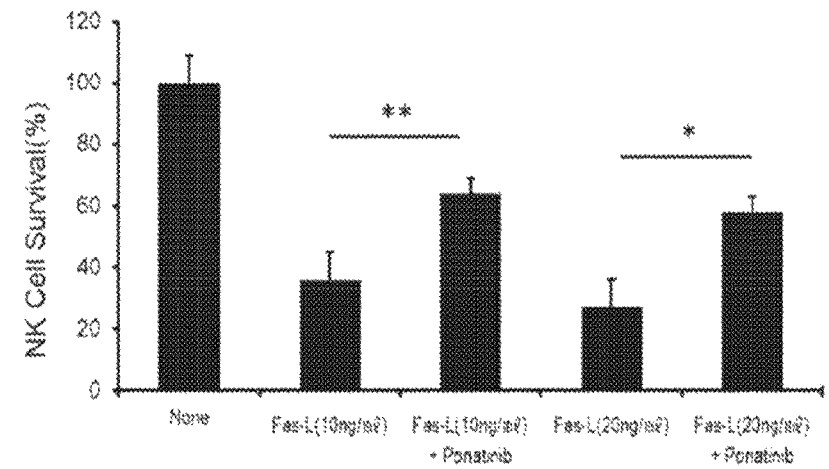
FIG. 1C is a graph showing survival percentages of NK cells pretreated with or without ponatinib, followed by treatment with Fas ligand (Fas-L).
Figure 9:
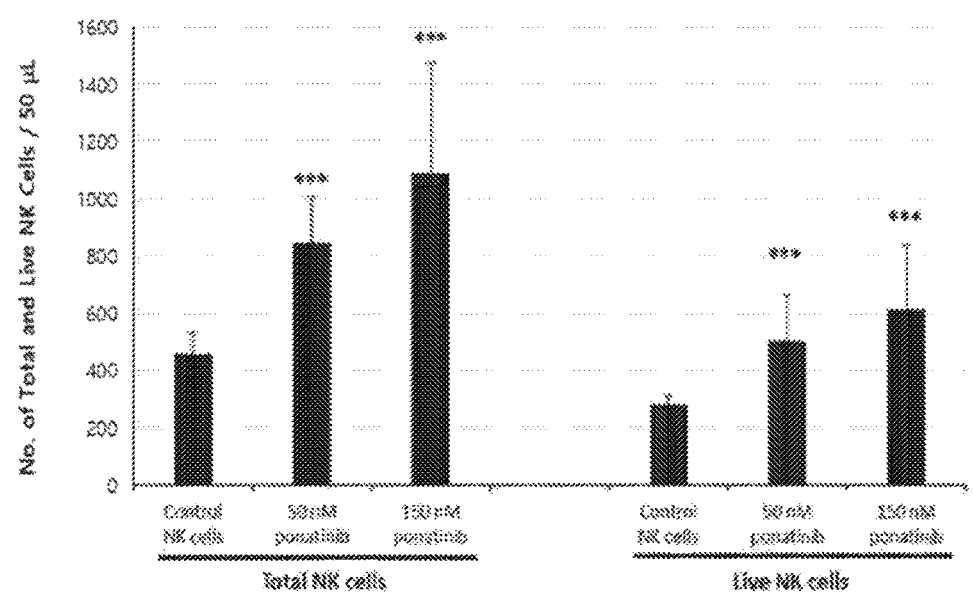
FIG. 9 is a graph showing in vivo cell number and survival of injected human NK cells with or without pre-treatment with ponatinib.
Figure 11C:
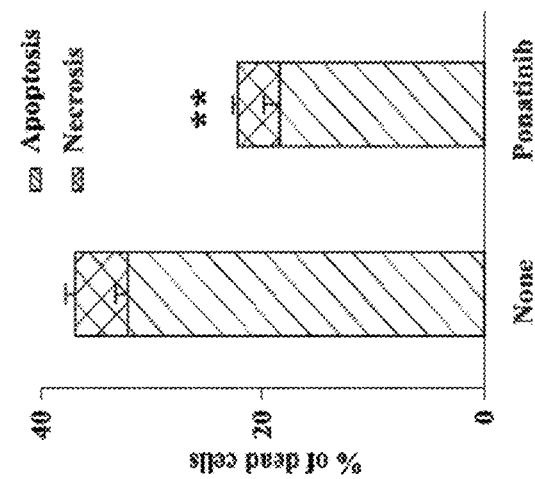
FIGS. 11A-C illustrate flow cytometry results showing annexin-V/7-AAD analysis result of NK cells pretreated with or without ponatinib.
Figure 11B:
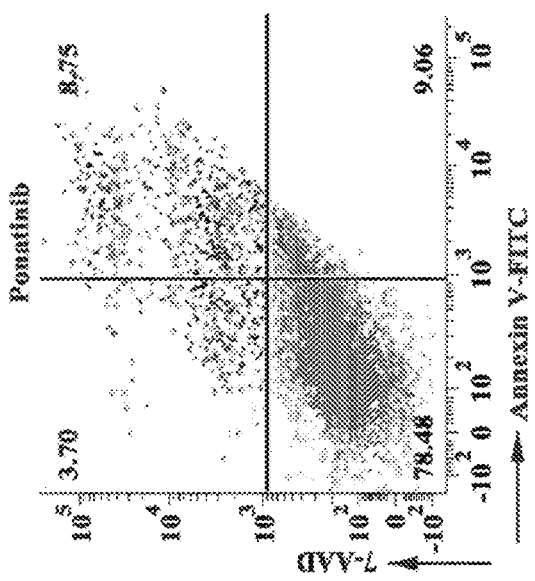
Figure 11A:
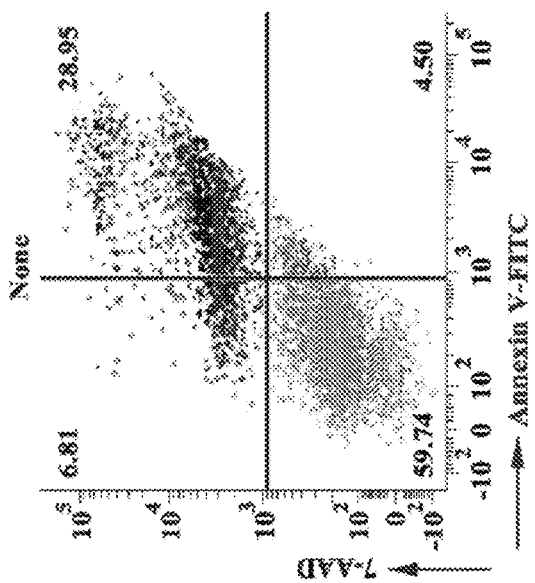
Figure 13C:
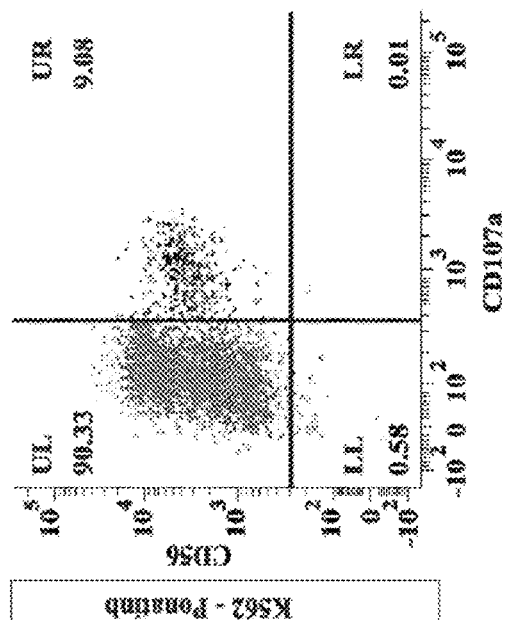
Figure 13D:
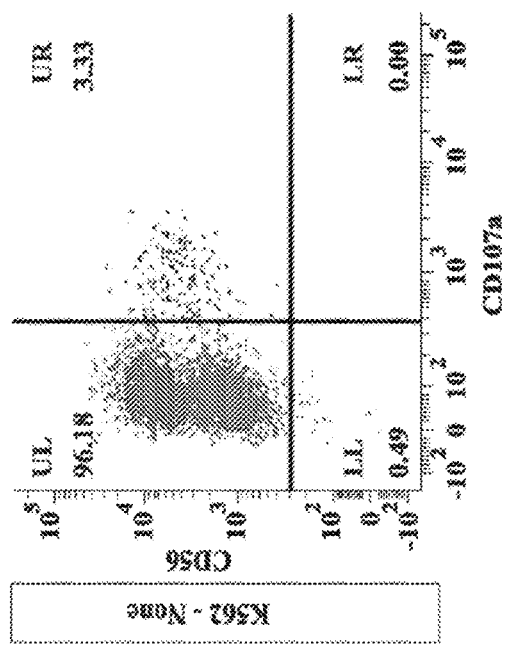

Treatment with TGF-β, FasL and sGITRL induced cell death of NK cells in a short time, but ponatinib pretreatment prevented the NK cell death caused by above mentioned cell death inducing substances, as shown in FIGS. 1A-C. Inventors examined whether ponatinib pretreatment can increase survival of NK cells both in vitro and in vivo. When human NK cells were injected into SCID mice, higher human NK cell number and viability were shown in mice injected with ponatinib pretreated NK cells than in mice injected with untreated NK cells, as shown in FIG. 9 and described further below. Also, pretreatment of ponatinib attenuated NK cell death after stimulation by co-culture with the target cancer cells, as shown in FIGS. 11A-C and described further below. Furthermore, flow cytometric analysis revealed that ponatinib pretreatment promotes growth of NK cells, as shown in FIGS. 11A-C and described further below. Considering the previous report that increasing cell numbers correlated with increased NK cell activity (Ohyashiki et al., Br J Haematol 157: 254-6, 2012), ponatinib might have the ability to increase the NK cell's anticancer activity.

Target cell lysis is mediated by cytotoxic molecules which are stored within secretory lysosomes, a specialized exocytic organelle, found in NK cells. Lysosomal-associated membrane protein-1 (LAMP-1 or CD107a) was shown to be a marker for NK cell cytolytic activity. Therefore, the inventors assessed whether CD107a expression is up-regulated on NK cells by pretreatment of ponatinib. The induction of CD107a expression was more pronounced when NK cells were exposed to ponatinib, as shown in FIGS. 13A-D and described further below. Therefore, ponatinib can increase the cytotoxic activity of NK cells by increasing cell viability and cell growth and CD107a expression of NK cells.

In some embodiments, pharmaceutical compositions comprising NK cells pretreated with ponatinib, and thereby rendered more resistant to apoptosis induced by sG sGITRL, TGF-β or Fas ligand (cell-death or apoptosis factors) and/or more cytotoxic to cancer cells, may be referred to herein as ponatinib-primed NK cells, or ponatinib-enhanced NK cells, or ponatinib-exposed NK cells, or CD107a-upregulated NK cells, or ponatinib-protected NK cells. Such references designate a population of NK cells having properties described herein (e.g., apoptosis resistance and enhanced cytotoxicity), but do not necessarily refer to NK cells made by any particular process (e.g., certain pre-treatment steps and conditions). Similarly, other immune cells rendered as more resistant to apoptosis factors, etc., by exposure to ponatinib are also compositions and not products-by-process.

EXAMPLES

FIGS. 1A-C are graphs showing survival percentage of NK cells pretreated with or without ponatinib, followed by treatment with various cell death-inducing substances according to some embodiments. FIGS. 1A-C show that pretreatment of NK cell with ponatinib significantly attenuated NK cell death induced by various cell death-inducing substances, such as sGITRL, TGF-β or Fas-L. Human NK cells were pretreated with or without ponatinib (150 nM) for 24 hrs, followed by treatment with sGITRL (1 or 5 ng/mL), TGF-β (2 or 5 ng/mL) or Fas-L (10 or 20 ng/mL) for 24 hrs. Then, NK cell survival (%) was obtained by dyeing NK cells with trypan blue, counting the number of surviving NK cells, and calculating a proportion of surviving NK cells in a treatment group to those in the control group. Results are presented as mean±SD of 3 independent experiments. The statistical difference was determined by one-way ANOVA. *$P<0.05$, $P<0.01$, *$P<0.005$.

As shown in FIG. 1A, there was no difference in survival rate of NK cells pretreated with ponatinib (ponatinib only) compared with that of control cells (None). Human NK cell death was induced by sGITRL in a dose dependent manner ($P<0.01$). Interestingly, pretreatment of ponatinib significantly inhibited sGITRL-induced NK cell death. Also, as shown in FIGS. 1B-C, when human NK cells were pretreated with ponatinib, TGF-β (2 or 5 ng/mL) or Fas-L (10 or 20 ng/mL)-induced NK cell death was significantly prevented. These results suggest that ponatinib has the ability to protect NK cell death induced by cell death-inducing substances.

Figure 1D:
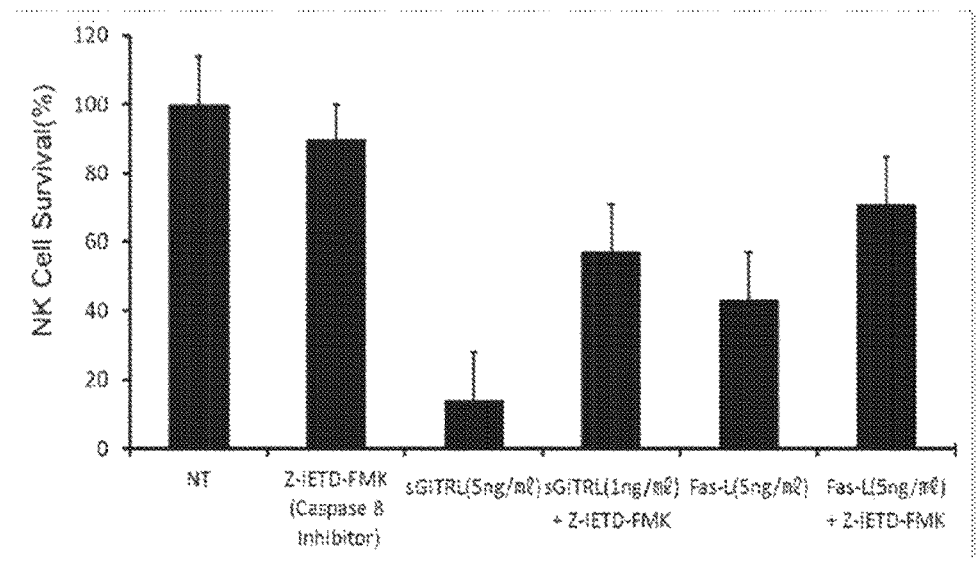
FIG. 1D is a graph showing survival percentages of NK cells pretreated with or without Z-IETD-FMK (caspase 8 inhibitor), followed by treatment with sGITRL or Fas-L.

FIG. 1D is a graph showing survival percentages of NK cells pretreated with or without Z-IETD-FMK, a capase 8 inhibitor, followed by treatment with sGITRL or Fas-L according to some embodiments. FIG. 1D shows that treating NK cells with caspase inhibitor before treating with sGITRL or Fas-L suppressed cell death induced by sGITRL or Fas-L and improved NK cell survival rate. When NK cells were cultured in media with 5 ng/mL of sGITRL or 5 ng/mL of Fas-L for two days, cell survival rate decreased due to cell death induced by sGITRL or Fas-L. Alternatively, NK cells were pretreated with Z-IETD-FMK (2 µM), an inhibitory peptide against apoptosis-related activity of Caspase 8, for 24 hours before being cultured in the media with sGITRL or Fas-L, and the number of surviving NK cells was analyzed and compared. Cell survival rate was also analyzed for NK cells treated with Z-IETD-FMK only.

Figure 1E:
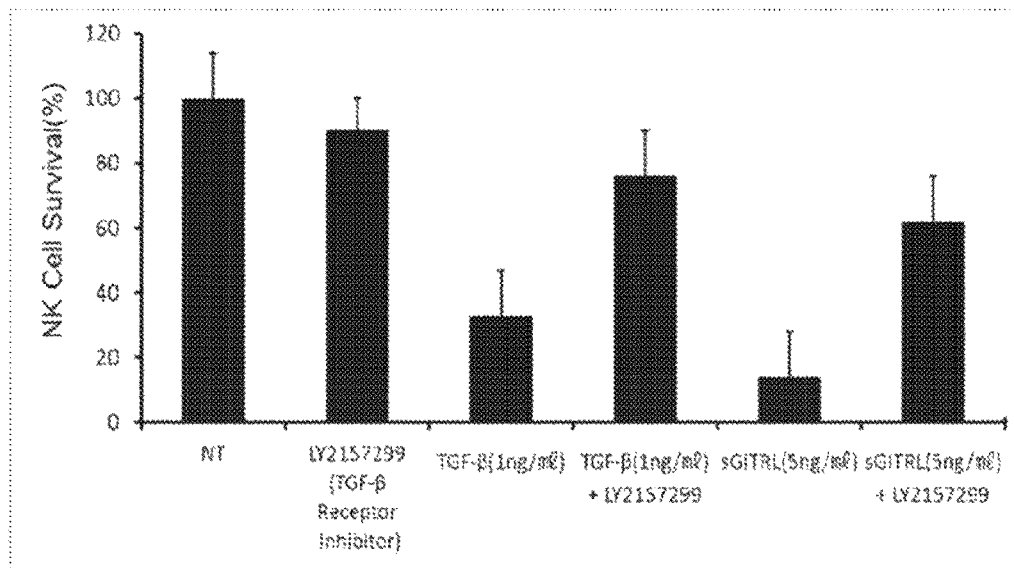
FIG. 1E is a graph showing survival percentages of NK cells pretreated with or without LY2157299 (TGF-β Receptor Inhibitor), followed by treatment with TGF-β.

FIG. 1E is a graph showing survival percentages of NK cells pretreated with or without LY2157299, a TGF-β receptor inhibitor, followed by treatment with TGF-β according to some embodiments. FIG. 1E shows that treating NK cells with TGF-β inhibitor before treating with TGF-β or sGITRL suppressed cell death induced by TGF-β or sGITRL and improved NK cell survival rate. When NK cells were cultured in media with 1 ng/mL of TGF-β or 5 ng/mL of sGITRL for two days, cell survival rate decreased due to cell death induced by TGF-β or sGITRL. Alternatively, NK cells were pretreated with LY2157299 (100 nM), a compound inhibiting kinases related to TGF-β receptor signaling, for 24 hours before being cultured in the media with TGF-β or sGITRL, and the number of surviving NK cells was analyzed and compared. Cell survival rate was also analyzed for NK cells treated with LY2157299 only.

FIG. 2A is a graph showing the viability of NK cells treated with various concentrations of ponatinib according to some embodiments, and shows the effect of ponatinib concentrations on cell viability of human NK cells. Human NK cells were exposed to various concentrations of ponatinib (30, 100, 200, 300, 500, 750, 1000 or 2000 nM) for 2 days and their viability was assayed by trypan blue staining. Results are presented as mean±SD of 4 independent cultures. The statistical difference was determined by one-way ANOVA. $P<0.01$, *$P<0.005$ (Without ponatinib (0) versus other groups). As shown in FIG. 2A, viability of human NK cells tended to be decreased at higher concentrations of ponatinib (from 1000 nM), indicating that high concentrations of ponatinib can induce NK cell death.

FIG. 2B is a graph showing the number of viable NK cells pretreated with various concentration of ponatinib, followed by treatment with sGITRL according to some embodiments. FIG. 2B shows that treating NK cells with ponatinib before treating with sGITRL suppressed cell death induced by sGITRL and increased the number of viable NK cells. When NK cells were pre-incubated with various concentrations of ponatinib (5, 20, 50, 100, 150, or 200 nM) for 16 hours, the number of viable NK cells did not significantly change after one day. When NK cells were cultured in media with 1 or 5 ng/mL of sGITRL for one day, the number of viable NK cells significantly decreased due to cell death induced by sGITRL. Then, NK cells were treated with various concentrations of ponatinib (5, 20, 50, 100, 150, or 200 nM) for 16 hours before being cultured in the sGITRL-treated media, and the number of viable NK cells was counted after trypan blue staining. Each concentration of ponatinib was treated to NK cells at $10^6$ cells/ml in a T-25 culture flask, and NK cell viability was tested after seeding $10^5$ cells/well in a 24-well culture plate. "NT" in FIG. 2 means no treatment of ponatinib.

FIG. 3 shows that pretreatment of ponatinib inhibited T cell death induced by sGITRL. Human T cells were exposed to DMSO (None) or Ponatinib (150 nM) for 24 hrs, followed by incubated with 5 ng/mL of sGITRL for 24 hrs. Survival rate of T cell was assayed by trypan blue staining. Results are presented as mean±SD of 3 independent experiments. The statistical difference was determined by one-way ANOVA. *$P<0.05$, **$P<0.01$. As expected, T cell death induced by sGITRL was attenuated by ponatinib pretreatment. There was no significant difference in T cell survival rate after ponatinib treatment.

Figures 4A, 4B:
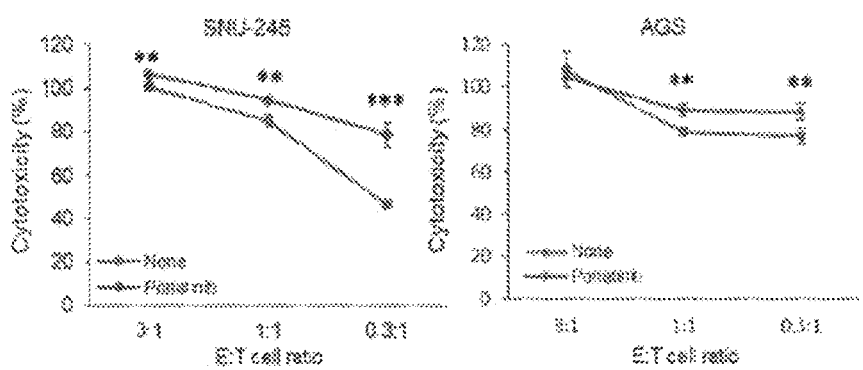
FIGS. 4A-B are graphs showing cytotoxic activity of NK cells pretreated with or without ponatinib against cancer cells (SNU-245, the biliary tract cancer cell line; AGS, the stomach cancer cell line).

FIGS. 4A-B are graphs showing cytotoxic activity of NK cells pretreated with or without ponatinib against cancer cells (SNU-245, the biliary tract cancer cell line; AGS, the stomach cancer cell line) according to some embodiments. FIGS. 4A-B show that pretreatment of ponatinib enhanced the cytotoxic activity of NK cells against cancers cells. Human NK cells were pretreated with ponatinib (150 nM) for 24 hrs and then washed before the cytotoxic activity assay against SNU-245 and AGS cells. NK cells (effector cells) were co-cultured with cancer cells (target cells; SNU-245 and AGS cells) at the effector-to-target (E:T) cell count ratio (3:1, 1:1, 0.3:1) for 4 hrs. Results are presented as mean±SD of 3 independent cultures. The statistical difference was determined by Student's t-test. *$P<0.05$, **$P<0.01$. As shown in FIGS. 4A-B, pretreatment of ponatinib in human NK cells strongly enhanced cytotoxicity against SNU-245 and AGS cells.

Figures 5A, 5B:
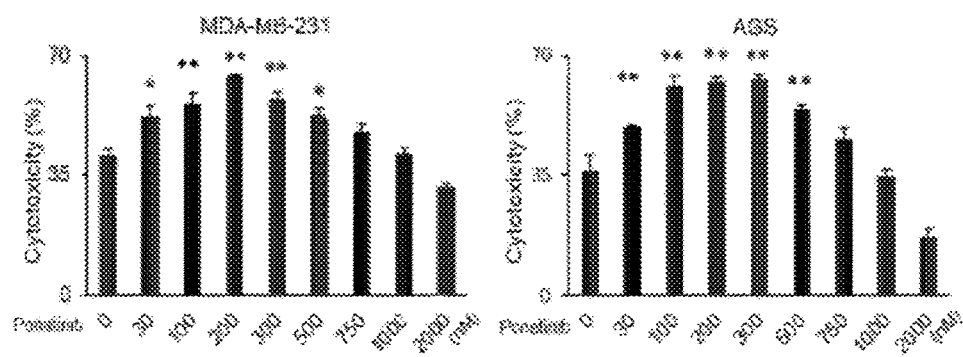
FIGS. 5A-B are graphs showing cytotoxic activity of NK cells pretreated with various concentrations of ponatinib against cancer cells (MDA-MB-231, the breast cancer cell line; AGS).

FIGS. 5A-B are graphs showing cytotoxic activity of NK cells pretreated with various concentrations of ponatinib against cancer cells (MDA-MB-231, the breast cancer cell line, AGS) according to some embodiments. FIGS. 5A-B show the effect of pretreated ponatinib concentrations on the cytotoxicity of NK cells against cancer cells. To estimate effective dose of ponatinib on cytotoxicity of NK cells, human NK cells were exposed to various concentration of ponatinib for 24 hrs. At the same time, MDA-MB-231 and AGS cells were plated into 96 well plate with 50-60% cell confluency and allowed to adhere to plates for 24 hrs. Human NK cells were then added to cancer cells at an E:T ratio of 0.5:1 for 2 days. All NK cells were then washed out from the plates and then viability of remaining cancer cells was analyzed by trypan blue staining. Cytotoxicity (%) was calculated as [100−(surviving cancer cells after NK treatment/non-treated cancer cells×100] (Mean±SD, N=3). Results are presented as mean±SD of 3 independent cultures. The statistical difference was determined by one-way ANOVA. *$P<0.05$, **$P<0.01$ (without ponatinib (0) versus other groups). As shown in FIGS. 5A-B, ponatinib-pretreated NK cells showed an increased cytotoxic activity against cancer cells at a ponatinib concentration range from 30 to 500 nM. However, cytotoxic activity of NK cells was decreased when high concentrations of ponatinib were pretreated, which might be due to the death of NK cells exposed to high concentrations of ponatinib, as described with regard to FIG. 2A.

FIGS. 6A-B are graphs showing cytotoxic activity of NK cells pretreated with various kinase inhibitors against cancer cells (AGS and MDA-MB-231 cells) according to some embodiments. NK cells were treated with each kinase inhibitor at the indicated concentrations for 24 hrs and then co-cultured with AGS (FIG. 6A) or MDA-MB-231 (FIG. 6B) cells at an E:T ratio of 0.5:1. After 48 hrs incubation, NK cells were washed out and the number of surviving cancer cells were counted. Cytotoxicity (%) was calculated as [100−(surviving cancer cells after NK treatment/non-treated cancer cells×100) (Mean±SD, N=3). Results are presented as mean±SD of 3 independent experiments. The statistical difference was determined by one-way ANOVA. ***P<0.005 (without Ponatinib (Non-treated) versus other groups). FIGS. 6A-B show that ponatinib pretreated NK cells had much higher cytotoxicity against cancer cells than NK cells treated with other kinase inhibitors.

Figure 7A:
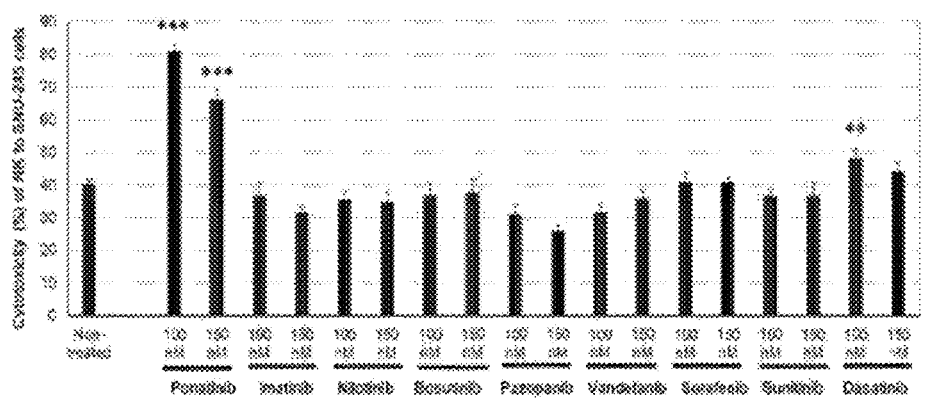
FIGS. 7A-B are graphs showing cytotoxic activity of NK cells pretreated with various kinase inhibitors against liver cancer cell lines (SNU-245 and SNU-387).
Figure 7B:
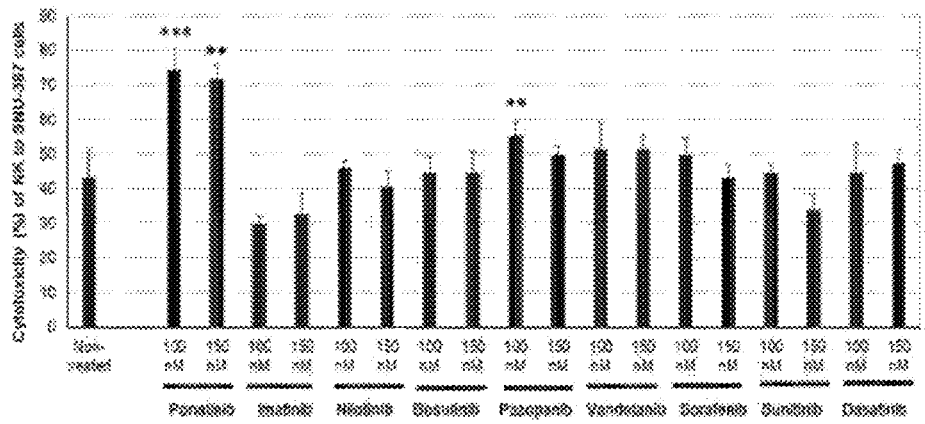

FIGS. 7A-B are graphs showing cytotoxic activity of NK cells pretreated with various kinase inhibitors against liver cancer cell lines (SNU-245 and SNU-387) according to some embodiments. FIGS. 7A-B show that ponatinib pretreated NK cells increased anti-cancer activity when compared with NK cells treated with other kinase inhibitors. NK cells were treated with each kinase inhibitor at the indicated concentrations for 24 hrs and then co-cultured with SNU-245 (FIG. 7A) and SNU-387 (FIG. 7B) cells at an E:T ration of 0.5:1. After incubation for 48 hrs, NK cells were washed out and the number of surviving cancer cells were counted. Cytotoxicity (%) was calculated as [100−(surviving cancer cells after NK treatment/non-treated cancer cells×100) (Mean±SD, N=3). Results are presented as mean±SD of 3 independent experiments. The statistical difference was determined by one-way ANOVA. P<0.01, *P<0.005 (without ponatinib (Non-treated) versus other groups). As shown in FIGS. 7A-B, dasatinib (FIG. 7A) or pazopanib (FIG. 7B) pretreated NK cells also showed increased cytotoxic activity compared to the untreated NK cells. However, cytotoxic activity against cancer cells was significantly higher in the ponatinib treated NK cells than in the other kinase inhibitors treated NK cells.

FIGS. 8A-C are graphs showing cytotoxic activity of ponatinib only and NK cells pretreated with or without ponatinib against various cancer cell lines (AGS, MDA-MB-231, and SNU-245) according to some embodiments. FIGS. 8A-C shows that ponatinib treatment alone did not show cytotoxicity against cancer cells. Cancer cells (MDA-MB-231, AGS and SNU-245 cells) were plated on 24 well plates and allowed them to adhere to plates for 24 hrs. NK cells were pretreated with ponatinib (150 nM) for 24 hrs prior to co-cultures with target cancer cells. Then NK cells were washed and incubated with targets cells at an E:T ration of 0.5:1 for 2 days. To examine whether ponatinib alone can induce cytotoxicity of cancer cells, it was added to cultures of target cells and then incubated for 2 days. Cytotoxicity (%) was calculated as [100−(surviving cancer cells after ponatinib treatment or NK treatment/non-treated cancer cells×100] (Mean±SD, N=3). Results are presented as mean±SD of 3 independent experiments. The statistical difference was determined by one-way ANOVA. *P<0.05, P<0.01, *P<0.005. As shown in FIGS. 8A-C, ponatinib treatment alone did not show cytotoxic activity against 3 different cancer cells, whereas viability of cancer cells co-cultured with NK cells pretreated with ponatinib was significantly decreased.

FIG. 9 is a graph showing in vivo cell number and survival of injected human NK cells with or without pretreatment with ponatinib according to some embodiments. FIG. 9 shows that human NK cells pretreated with ponatinib exhibited an elevated survival in vivo. Human NK cells were treated with or without ponatinib (50 or 150 nM) for 24 hrs and stained with carboxyfluorescein succinimidyl ester (CFSE), and then 2×10$^7$ cells were injected into 10 SCID mice per each group via tail vein. One day after injection, blood was taken from the eye vein and total human NK cells or live human NK cells were counted using a flow cytometer. The statistical difference was determined by one-way ANOVA. ***P<0.005 (Control NK cells versus other groups). As shown in FIG. 9, the mice injected with ponatinib treated NK cells have more human NK cells and higher viability than the mice injected with non-treated NK cells.

Figures 10A, 10B, 10C:
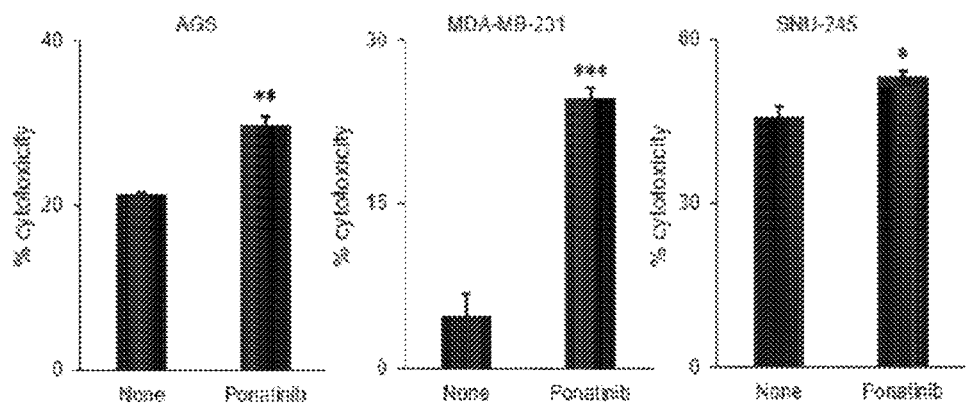
FIGS. 10A-C are graphs showing the cytotoxic activity of NK cells with or without ponatinib against cancer cell lines.

FIGS. 10A-C are graphs showing the cytotoxic activity of NK cells with or without ponatinib against cancer cell lines according to some embodiments. FIGS. 10A-C shows that formulated NK cells with ponatinib increased cytotoxicity of NK cells against cancer cells. To determine whether ponatinib could increase the cytotoxic potency of NK cells in a therapeutic formulation, human NK cell products were stored in therapeutic formulations with or without ponatinib for 24 hrs. Cancer cells (AGS, MDA-MB-231 and SNU-245 cells) were plated on 24 well plates and allowed to adhere to plates for 24 hrs. Then, formulated NK cells containing ponatinib were incubated with cancer cells at an E:T ration of 0.5:1 for 2 days, as previously described. Results are presented as mean±SD of 3 independent experiments. The statistical difference was determined by Student's t-test. *P<0.05, P<0.01, *P<0.005. As shown in FIGS. 10A-C, the formulated NK cells containing ponatinib have shown greater cytotoxicity against the cancer cells than NK cells alone.

FIGS. 11A-C illustrate flow cytometry results showing annexin-V/7-AAD analysis result of NK cells pretreated with or without ponatinib. FIGS. 11A-C show that increased cytotoxicity of NK cells by ponatinib pretreatment was mediated by enhanced viability of NK cells. To examine by which ponatinib pretreatment influenced on the improvement of cytotoxic activity of NK cells, Annexin V/7-AAD analysis was performed with NK cells co-cultured with cancer cells. NK cells were pretreated with or without ponatinib (150 nM) for 24 hrs and then incubated with K562 cells at an E:T ratio of 5:1 for 4 hrs. After incubation, NK cells were collected and analyzed for cell death by annexin-V and 7-AAD analysis. As shown in Figure, both apoptotic [Annexin V$^+$/7-AAD$^-$ and Annein V$^+$/7-AAD$^+$) and necrotic cell population (Annexin V$^-$/7-AAD$^+$) were significantly reduced in cells pretreated with ponatinib compared with those in untreated cells. Dot plots of a representative sample were shown in FIGS. 11A-B. Results are presented as mean±SD of 3 independent experiments. The statistical difference was determined by Student's t-test. **P<0.01.

FIGS. 12A-C illustrate flow cytometry results showing the fraction distributed at G0/G1, S and G2/M phases in NK cells treated with or without ponatinib. FIGS. 12A-C shows that ponatinib pretreatment up-regulates NK cell cycle progression. To examine the effects of ponatinib on NK cell growth in vitro, cell cycle analysis was performed by propidium iodide (PI) staining that is used to analyze DNA cell cycle and then by flow cytometry. Human NK cells were incubated with ponatinib (150 nM) for 2 days. After staining the NK cells with P, flow cytometry was performed. Histograms in Figure show the fraction distributed at G0/G1, S and G2/M phases in NK cells treated with or without ponatinib. Ponatinib treatment increased the fraction of S and G2/M phases of NK cells with a concomitant decrease in the fraction of G0/G1 phases, compared to control NK cells, suggesting that ponatinib increased the proliferation of NK cells. Results are presented as mean±SD of 3 independent experiments. The statistical difference was determined by Student's t-test. **P<0.01.

FIGS. 13A-D illustrate flow cytometry results showing ponatinib pretreated NK cell degranulation against K562 targets according to some embodiments. To explore whether the increased cytotoxicity of NK cells against cancer cells by Ponatinib pretreatment is mediated by increased granulation of NK cells, NK cell degranulation assay was performed. Briefly, NK cells treated with or without Ponatinib were plated in 96 well U-bottom plates at 1×10$^6$ cells/well in the presence an alliphcocyanin (APC)-labeled monoclonal antibody (mAb) against CD107a. The anti-CD107a mAb was kept in the medium throughout the stimulation period because CD107a that has been externalized by NK cells upon degranulation is rapidly reinternalized. Degranulation of NK cells was induced by adding K562 target cells (5×10$^5$ per well, E:T ratio=2:1) or phorbol 12-myristate 13-acetate plus ionomycin (PMA+ION) as positive control and then by incubating for 5 hrs. A negative control is cells without degranulation stimuli. And then Monensin was added to the cultured cells and incubated for 3 hrs to block intracellular protein transport. The cells were then washed and stained with a fluorescein isothiocyanate (FITC)-labeled anti-CD56 mAb. As shown in FIGS. 13A-D, the results showed that ponatinib pretreatment triggered NK cell degranulation against K562 targets.

Table 1 shows that pretreatment of NK cells with ponatinib improved anti-cancer activity of NK cells against various blood cancer cells. NK cells were treated with ponatinib (500 nM) for 6 hrs and then co-cultured with cancer cells such as THP-1 (acute monocyte leukemia), HL-60 (acute promyelocytic leukemia), or KG-1 (acute myelogenous leukemia) cells for 48 hours. Then, cytotoxicity of NK cells against cancer cells in these experimental groups was measured by comparing the number of surviving cancer cells in the experimental groups to that in the control group, in which untreated NK cells were co-cultured with cancer cells. IL-2 is a well-known activator of effector cells such as NK cells. Treating NK cells with IL-2 increased the killing activity of NK cells, and treatment of NK cells with ponatinib further increased cytotoxicity of IL2-activated NK cells.

TABLE 1

Cytotoxicity* of NK Cells to Leukemia Cells

| | | THP-1 Cells | | HL-60 Cells | | KG-1 Cells | |
|---|---|---|---|---|---|---|---|
| | Ponatinib Treatment | Without IL-2 | With IL-2 | Without IL-2 | With IL-2 | Without IL-2 | With IL-2 |
| E:T = 1:1 ** | NT*** | 64 ± 1 | 97 ± 2 | 46 ± 5 | 99 ± 0 | 94 ± 1 | 95 ± 3 |
| | 500 nM | 83 ± 1 | 99 ± 0 | 89 ± 4 | 98 ± 2 | 99 ± 1 | 99 ± 1 |
| E:T = 0.1:1 | NT | 5 ± 4 | 46 ± 4 | 1 ± 3 | 42 ± 0 | 33 ± 6 | 80 ± 8 |
| | 500 nM | 20 ± 1 | 79 ± 4 | 13 ± 3 | 76 ± 9 | 81 ± 1 | 93 ± 1 |

*Cytotoxicity(%) = [1 − (surviving cells after NK cell treatment/non-treated cancer cells)] × 100, Mean ± SD, N = 3
** Effector (NK cells) to target (leukemia cancer cells) ratio
***Non-treated NK cells Table 2 shows that pretreatment of NK cells with ponatinib improved anti-cancer activity of NK cells against solid cancers. NK cells were treated with 50 nM (for MDA-MB-231) or 200 nM (for MIA PaCa-2) of ponatinib for 6 hrs and then co-cultured with MDA-MB-231 (breast cancer) or MIA PaCa-2 (pancreatic cancer) cells for 48 hrs. Then, cytotoxicity of NK cells in these experimental groups was measured by comparing the number of surviving cancer cells in the experimental groups to that in the control group, in which untreated NK cells were co-cultured with cancer cells. Treating NK cells with IL-2 increased the killing activity of NK cells, and treating NK cells with ponatinib further increased cytotoxicity of IL2-activated NK cells.

TABLE 2

Cytotoxicity* of NK Cells to Solid Tumor Cells

| | | MDA-MB-231 Cells | | MIA PaCa-2 Cells | |
|---|---|---|---|---|---|
| | Ponatinib Treatment | Without IL-2 | With IL-2 | Without IL-2 | With IL-2 |
| E:T = 0.5:1** | Non-treated | 33 ± 3 | 45 ± 4 | 61 ± 9 | 82 ± 4 |
| | Treated*** | 54 ± 8 | 59 ± 8 | 78 ± 2 | 100 ± 0 |
| E:T = 0.1:1 | Non-treated | 12 ± 8 | 7 ± 10 | 26 ± 9 | 52 ± 4 |
| | Treated*** | 34 ± 4 | 28 ± 5 | 43 ± 8 | 66 ± 5 |

*Cytotoxicity (%) = [1 − (surviving cells after NK cell treatment/non-treated cancer cells)] × 100, Mean ± SD, N = 3
**Effector (NK cells) to target (solid tumor cells) ratio
***For MDA-MB-231 cells, NK cells were treated with 50 nM Ponatinib and for MIA PaCa-2 cells, with 200 nM Ponatinib.

Table 3 shows a prophetic example that treating NK cells with caspase inhibitor improves anti-cancer activity of NK cells against solid cancer. NK cells are treated with Z-IETD-FMK (2 μM), an inhibitory peptide against apoptosis-related activity of Caspase-8, for 24 hours and then co-cultured with NCI-H1299 (lung cancer) or PC-3 (prostate cancer) cells for 48 hours. Then, cytotoxicity of NK cells in these experimental groups are measured by comparing the number of surviving cancer cells in the experimental groups to that in the control group, in which untreated NK cells are co-cultured with cancer cells. Treating NK cells with IL-2 increases the killing activity of NK cells, and treating NK cells with Z-IETD-FMK further increases cytotoxicity of IL2-activated NK cells.

TABLE 3

Cytotoxicity* Changes of NK Cells to Solid Tumor Cells after Treatment of Apoptosis Inhibitor.

| Caspase-8 Inhibitor | | NCI-H1299 Cells | | PC-3 Cells | |
|---|---|---|---|---|---|
| | | Without IL-2 | With IL-2 | W/O IL-2 | W/ IL-2 |
| E:T = 0.5:1** | Non-treated | 22 | 35 | 56 | 81 |
| | 2 µM Treated | 34 | 58 | 78 | 96 |
| E:T = 0.1:1 | Non-treated | 12 | 23 | 29 | 54 |
| | 2 µM Treated | 25 | 33 | 48 | 76 |

*Cytotoxicity (%) = [1 − (surviving cells after NK cell treatment/non-treated cancer cells)] × 100, Mean, N = 3
**Effector (NK cells) to target (solid tumor cells) ratio Table 4 shows a prophetic example that treating NK cells with TGF-β receptor inhibitor improves anti-cancer activity of NK cells against solid cancer. NK cells are treated with LY2157299 (100 nM), a compound inhibiting kinases related to TGF-β receptor signaling, for 24 hours and then co-cultured with SK-4 (stomach cancer) or HCT-15 (colon cancer) cells for 48 hours. Then, cytotoxicity of NK cells in these experimental groups are measured by comparing the number of surviving cancer cells in the experimental groups to that in the control group, in which untreated NK cells are co-cultured with cancer cells. Treating NK cells with IL-2 increases the killing activity of NK cells, and treating NK cells with LY2157299 further increases cytotoxicity of IL2-activated NK cells.

TABLE 4

Cytotoxicity* Changes of NK Cells to Solid Tumor Cells after Treatment of TGF-β Receptor Inhibitor.

| TGF-β Receptor Inhibitor | | SK-4 Cells | | HCT-15 Cells | |
|---|---|---|---|---|---|
| | | Without IL-2 | With IL-2 | W/O IL-2 | W/ IL-2 |
| E:T = 05:1** | Non-treated | 24 | 37 | 59 | 84 |
| | 100 nM Treated | 35 | 59 | 82 | 98 |
| E:T = 0.1:1 | Non-treated | 13 | 26 | 33 | 57 |
| | 100 nM Treated | 27 | 39 | 68 | 86 |

*Cytotoxicity (%) = [1 − (surviving cells after NK cell treatment/non-treated cancer cells)] × 100, Mean, N = 3
**Effector (NK cells) to target (solid tumor cells) ratio Table 5 shows a prophetic example that treating NK cells with kinase inhibitor improves cytotoxic activity of NK cells against virally transformed cells. NK cells are treated with ponatinib (150 nM), a multiple-targeted kinase inhibitor, for 16 hours and then co-cultured with HepG2.2.15 (hepatic cell transformed with hepatitis B virus and producing HBV) or Huh-7.5 (hepatic cell line showing subgenomic and genomic hepatitis C virus RNA replication) cells for 48 hours. Then, cytotoxicity of NK cells in these experimental groups are measured by comparing the number of surviving virally transformed cells in the experimental groups to that in the control group, in which untreated NK cells are co-cultured with virally transformed cells. Treating NK cells with IL-2 increases the killing activity of NK cells, and treating NK cells with ponatinib further increases cytotoxicity of IL-2-activated NK cells.

TABLE 5

Cytotoxicity* Changes of NK Cells to Virus-Transformed Cell Lines after Treatment of a Kinase Inhibitor.

| Ponatinib (Kinase Inhibitor) | | HepG2.2.15 Cells | | Huh-7.5 Cells | |
|---|---|---|---|---|---|
| | | Without IL-2 | With IL-2 | W/O IL-2 | W/IL-2 |
| E:T = 0.5:1** | Non-treated | 52 | 65 | 56 | 81 |
| | 150 nM Treated | 74 | 88 | 78 | 96 |
| E:T = 0.1:1 | Non-treated | 42 | 43 | 29 | 54 |
| | 150 nM Treated | 59 | 75 | 48 | 76 |

*Cytotoxicity (%) = [1 − (surviving cells after NK cell treatment/non-treated virally transformed cells)] × 100, Mean, N = 3
**Effector (NK cells) to target (solid tumor cells) ratio

Terminology

The foregoing description of the exemplary embodiments has been presented only for the purposes of illustration and description and is not intended to be exhaustive or to limit the invention to the precise forms disclosed. Many modifications and variations are possible in light of the above teaching. It is contemplated that various combinations or sub combinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the invention is defined by the appended claims rather than the foregoing description and the exemplary embodiments described therein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The ranges disclosed herein also encompass any and all overlap, sub-ranges, and combinations thereof. Language such as "up to," "at least," "greater than," "less than," "between," and the like includes the number recited.

Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

The term "generally" as used herein represents a value, amount, or characteristic that predominantly includes or tends toward a particular value, amount, or characteristic. As an example, in certain embodiments, the term "generally uniform" refers to a value, amount, or characteristic that departs from exactly uniform by less than 20%, less than 15%, less than 10%, less than 5%, less than 1%, less than 0.1%, and less than 0.01%.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 5.0 cm" includes "5.0 cm."

Some embodiments have been described in connection with schematic drawings. However, it should be understood that the schematic drawings are not drawn to scale. Distances are merely illustrative and do not necessarily bear an exact relationship to actual dimensions and layout of the devices illustrated.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A pharmaceutical composition for treating cancer, the pharmaceutical composition comprising:
   immune cells, wherein the immune cells comprise NK cells and/or T cells; and
   ponatinib or a pharmaceutically acceptable salt or derivative thereof.

2. The pharmaceutical composition of claim 1, wherein the immune cells comprise NK cells, wherein NK cells comprise at least one of NK cells cultured with cytokines; NK cells co-cultured with cytokines and irradiated human peripheral blood mononuclear cells (PBMC); NK cells co-cultured with established cell line(s) or genetically engineered feeder cells or both; and genetically engineered CAR-NK cells.

3. The pharmaceutical composition of claim 2, wherein the established cell lines are transformed lymphocyte cells selected from LCL cells, KL-1 cells, or K562 cells.

4. The pharmaceutical composition of claim 1, wherein the immune cells comprise T cells, wherein T cells comprise at least one of T cells isolated from peripheral blood mononuclear cells (PBMC) and cultured with cytokines; T cells extracted near tumors; T cells treated with activators; and genetically engineered CAR-T cells.

5. The pharmaceutical composition of claim 1, wherein the concentration of ponatinib or pharmaceutically acceptable salt or derivative thereof is from about 1 nM to 1 µM.

6. The pharmaceutical composition of claim 1, wherein said immune cells are pre-treated with an effective amount of ponatinib or pharmaceutically acceptable salt or derivative thereof.

7. The pharmaceutical composition of claim 6, wherein said immune cells are pre-treated with ponatinib or pharmaceutically acceptable salt or derivative thereof at a concentration of about 1 nM to 1 M.

8. The pharmaceutical composition of claim 1, wherein the immune cells comprise NK cells.

9. A pharmaceutical composition for treating cancer, the pharmaceutical composition comprising immune cells, wherein the immune cells comprise NK cells and/or T cells, wherein the immune cells are expanded in vitro and then treated with an effective concentration of ponatinib or a pharmaceutically acceptable salt or derivative thereof, wherein the pharmaceutical composition comprises about $10^5$ to about $10^{11}$ of the immune cells that have been treated with the ponatinib or pharmaceutically acceptable salt or derivative thereof.

10. The pharmaceutical composition of claim 9, wherein the immune cells comprise NK cells selected from the group consisting of at least one of:
    genetically engineered CAR-NK cells;
    NK cells cultured with cytokines;
    NK cells co-cultured with cytokines and irradiated human peripheral blood mononuclear cells (PBMC);
    NK cells co-cultured with an established cell line; and
    NK cells co-cultured with genetically engineered feeder cells.

11. The pharmaceutical composition of claim 10, wherein the established cell line is a transformed lymphocyte.

12. The pharmaceutical composition of claim 11, wherein the transformed lymphocyte is selected from the group consisting of at least one of: LCL cells, KL-1 cells, and K562 cells.

13. The pharmaceutical composition of claim 9, wherein the immune cells comprise T cells, wherein T cells comprise at least one of T cells isolated from peripheral blood mononuclear cells (PBMC) and cultured with cytokines; T cells extracted near tumors; T cells treated with activators; and genetically engineered CAR-T cells.

14. The pharmaceutical composition of claim 9, wherein the effective concentration of ponatinib or a pharmaceutically acceptable salt or other derivative thereof is about 1 nM to 1 µM.

15. The pharmaceutical composition of claim 9, wherein the immune cells comprise NK cells.

16. A method for treating cancer, comprising administering an effective amount of the pharmaceutical composition of claim 9 to a patient in need thereof.

17. A method for treating cancer, the method comprising:
proliferating immune cells in vitro before treating the immune cells with ponatinib or a pharmaceutically acceptable salt or derivative, wherein the immune cells comprise NK cells and/or T cells; and
administering an effective amount of a pharmaceutical composition comprising the treated immune cells to a patient, wherein the pharmaceutical composition comprises about $10^5$ to about $10^{11}$ treated immune cells per dose.

18. The method of claim 17, further comprising collecting immune cells from a subject before treating the immune cells with ponatinib.

19. The method of claim 18, wherein the subject is the patient.

20. The method of claim 17, wherein administering the pharmaceutical composition comprises intravenously injecting the pharmaceutical composition.

21. The method of claim 17, wherein the concentration of ponatinib or pharmaceutically acceptable salt thereof is about 1 nM to 1 µM.

22. The method of claim 17, wherein the pharmaceutical composition comprises about $10^5$ to about $10^{10}$ treated immune cells per dose.

23. The method of claim 17, wherein the immune cells comprise NK cells.

24. The method of claim 17, further comprising isolating the immune cells from peripheral blood.

25. The method of claim 17, wherein the pharmaceutical composition further comprises ponatinib or a pharmaceutically acceptable salt or derivative thereof.

* * * * *